United States Patent [19]

Matsumoto

[11] Patent Number: 4,705,764

[45] Date of Patent: Nov. 10, 1987

[54] ESTERIFICATION AND/OR ESTER INTERCHANGE CATALYST

[75] Inventor: Satoshi Matsumoto, Kumamoto, Japan

[73] Assignee: Research Development Corporation of Japan, Japan

[21] Appl. No.: 912,427

[22] Filed: Sep. 26, 1986

[30] Foreign Application Priority Data

Oct. 3, 1985 [JP] Japan ............................... 60-219140
Dec. 14, 1985 [JP] Japan ............................... 60-280220
Jun. 10, 1986 [JP] Japan ............................... 61-132618

[51] Int. Cl.$^4$ .......................... B01J 31/06; B01J 31/02
[52] U.S. Cl. ..................................... 502/62; 502/171; 556/54
[58] Field of Search ...................... 502/62, 171; 556/54

[56] References Cited

U.S. PATENT DOCUMENTS

| | | | |
|---|---|---|---|
| 2,643,262 | 6/1953 | Bostwick ............................. | 252/56 |
| 3,047,515 | 7/1962 | Piirma ............................... | 556/54 X |
| 3,121,109 | 2/1964 | Young ............................... | 556/54 X |
| 3,177,194 | 4/1965 | Stampa .............................. | 556/54 X |
| 3,194,764 | 7/1965 | Ovist et al. ......................... | 260/429 |
| 4,506,091 | 3/1985 | Deardorff ............................ | 560/99 |
| 4,513,095 | 4/1985 | Speca ............................... | 502/171 X |
| 4,524,201 | 6/1985 | Barnabeo et al. ................. | 556/54 X |

FOREIGN PATENT DOCUMENTS 53-94296  8/1978  Japan .

OTHER PUBLICATIONS

*Chemical Abstracts*, vol. 101, No. 131919H, 1984.

Primary Examiner—Patrick P. Garvin
Attorney, Agent, or Firm—Lowe, Price, Leblanc, Becker & Shur

[57] ABSTRACT

Esterification and/or ester interchange reaction catalysts composed respectively of a highly-crosslinked polyol polytitanate, a highly-crosslinked high-molecular polytitanate and a polyol polytitanate having the polytitanic acid structure as well as processes for their preparation.

18 Claims, No Drawings

ESTERIFICATION AND/OR ESTER INTERCHANGE CATALYST

BACKGROUND OF THE INVENTION

1. Field of the Invention

This invention relates to high-activity solid catalysts suitable for use in esterification reactions and/or ester interchange reactions and preparation processes thereof.

2. Description of the Prior Art

Catalysts, for example, organic acids such as p-toluenesulfonic acid, inorganic acids such as sulfuric acid and hydrochloric acid, alkalies, and tetraalkoxy titaniums have conventionally been used for esterification reactions and ester interchange reactions. These reactions are widely used in the industry. For instance, useful resin plasticizers such as dioctyl phthalate (hereinafter abbreviated as "DOP") and dioctyl adipate (hereinafter abbreviated as "DOA") are produced industrially by esterification reactions. Their production is however accompanied by problems as will be described next.

Catalysts employed in these industrial esterification reactions are of course required to have practical and high activities. It is however very difficult to achieve the reactions between acids and their corresponding alcohols to approximately 100%. It may be contemplated to use these catalysts in large amounts with a view to accelerating the reaction velocities. The removal of catalyst residue gives more problem as such catalysts are employed in larger amounts. In order to improve the electrical characteristics, thermal stability and the like of plastic compositions with plasticizers incorporated therein, it is essential to remove still-remaining unreacted acids to an acid value of 0.1 or even lower. Such a low acid value is also required in various specifications. To this end, there is also an outstanding demand for high-activity catalysts which exhibit high activities even at low concentrations. In the case of p-toluenesulfonic acid catalyst, its catalytic activities are sufficiently high even at low temperatures but it is accompanied by a drawback in the removal of catalyst residue. On the other hand, alkoxy titanium catalysts are accompanied by the same drawback as acid catalysts. Namely, neutralization and water-rinsing steps are indispensable unless acid values are lowered significantly by the removal of catalyst residue (inclusive of removal of the catalysts through their decomposition). This neutralization step however leads to another problem that the remaining acid is converted to a salt and hence acts as a surfactant, thereby making it difficult to separate the aqueous mixture into an ester layer and water layer. As the acid becomes more complex, its removal becomes more difficult so that the product of the esterification reaction cannot be treated to a low acid value.

As a method for the removal of catalyst residue of a titanium catalyst, it has recently been proposed to employ a chelating agent (U.S. Pat. No. 4,506,091). Researches are also under way to provide heterogeneous solid catalysts, which permit minimized dissolution of their catalytic components in reaction systems.

For example, an esterification catalyst supported on a carrier has been proposed [Chemical Abstracts, 131919h (1984)]. Similar to conventional catalysts, this catalyst however requires removal of its acid component by washing it with an alkaline solution after conducting an esterification reaction fully. It is hence not satisfactory. As titanium catalysts of the heterogeneous system which feature minimized loss due to their dissolution in esterification reactions and hence permit their use in small amounts, there have been proposed certain catalysts including that obtained by treating a polymer of a tetraalkoxy titanate hydrolytically with a peroxide in the presence of an alkali and then treating the thus-treated polymer under reflux in a monohydric alcohol such as n-butyl alcohol or heptanol (Japanese Patent Laid-Open No. 94296/1978). They are however accompanied by one or more shortcomings that their preparation processes are complex and/or difficulties are encountered in imparting catalytic properties most suitable for various esterification reactions In U.S. Pat. Nos. 3,194,764 and 2,643,262 referred to in the former U.S. patent, it is also disclosed to use the reaction product (glycol titanate) of an orthotitanate and glycol as a catalyst upon preparation of a mixed ester, which is useful as a synthetic lube oil, from a monohydric alcohol, dicarboxylic acid and glycol. These patent publications also disclose that the properties of the glycol titanate are in between those of monomeric glycol titanate and those of polymeric glycol titanates, it is in a liquid or solid form, and moreover, it has compatibility with the reaction system (solubility, miscibility, dispersibility). It is also disclosed that the catalytically-active component is a chelate compound with the hydroxyl groups of the glycol, which was employed upon preparation of the catalyst, coordinated about a titanium atom, although the structure of the catalytically-active component is said not to be fully elucidated. When an esterification reaction is conducted by using the above catalyst system, its catalytic activities are however not satisfactory due to its insufficient insolubilization and crosslinking degree, thereby failing to provide an esterification reaction product of a low acid value.

SUMMARY OF THE INVENTION

An object of this invention is to provide a novel, high-activity, titanium catalyst of the heterogeneous system, which has improved the abovedescribed drawbacks of conventional esterification and/or ester interchange catalysts and can reduce the acid value of reaction products to extremely low levels.

In one aspect of this invention, there is thus provided an esterification and/or ester interchange catalyst which comprises a highly-crosslinked polyol polytitanate.

In another aspect of this invention, there is also provided a process for the preparation of a highly-crosslinked polyol polytitanate useful as an esterification and/or ester interchange catalyst, which comprises reacting an alkoxy titanium and a polyol and then subjecting the reaction product to dealcoholization so as to have the reaction product be crosslinked to a high degree.

In a further aspect of this invention, there is also provided an esterification and/or ester interchange catalyst which comprises a highly-crosslinked high-molecular polytitanate.

In a still further aspect of this invention, there is also provided a process for the preparation of an esterification and/or ester interchange catalyst composed of a highly-crosslinked high-molecular polytitanate, which comprises subjecting the reaction product of an alkoxy titanium and water to dealcoholization.

In a still further aspect of this invention, there is also provided an esterification and/or ester interchange catalyst which comprises a polyol polytitanate having the polytitanic acid structure.

In a still further aspect of this invention, there is also provided a process for the preparation of an esterification and/or ester interchange catalyst composed of a polyol polytitanate having the polytitanate structure, which comprises reacting the reaction product of an alkoxy titanium and a polyol or water with water or a polyol so as to convert said reaction product into a highly-crosslinked high-molecular product through dealcoholization, and then subjecting the high-molecular product to a water treatment to convert the same into a hydrate thereof.

In a still further aspect of this invention, there is also provided a process for the preparation of an esterification or ester interchange catalyst composed of a polyol polytitanate having the polytitanate structure, which comprises reacting the reaction product of an alkoxy titanium of a lower alcohol, a monohydric higher alcohol and a polyol with water, subjecting the reaction product to dealcoholization so as to convert said reaction product into a highly-crosslinked high-molecular product, and then subjecting the high-molecular product to a water treatment to convert the same into a hydrate thereof.

The esterification and/or ester interchange catalyst of the present invention, which is composed of a highly-crosslinked polyol polytitanate, a highly-crosslinked high-molecular polytitanate or a polyol polytitanate having the polytitanic acid structure respectively, can reduce the acid value of the reaction product to an extremely low level. This has an extremely great industrial significance. Moreover, the removal of catalyst residue (solid) requires simple filtration only. Since the reaction product produced by an esterification reaction or ester interchange reaction in the presence of the catalyst of this invention has an extremely low acid value, it is possible to omit the washing step for the reaction product.

The above and other objects, features and advantages of the present invention will become apparent from the following description and the appended claims.

DETAILED DESCRIPTION OF THE INVENTION

(Highly-Crosslinked Polyol Polytitanates)

In the thought that if a polyol polytitanate represented by the following formula can be prepared, it can be insolubilized in the reaction system (reaction mixture) of an esterification reaction and the removal of catalyst residue can be achieved by mere filtration by converting said polyol polytitanate into a crosslinked high-molecular product, the present inventor has proceeded with an intensive investigation.

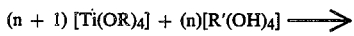

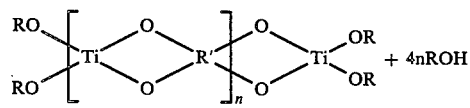

wherein R means a monohydric alcohol residue, R' denotes a polyhydric alcohol residue, and the above reaction formula indicates a reaction with a tetrahydric alcohol.

Namely, a polyol titanate seems to occur by the above formula with simultaneous formation of an alcohol in a stoichiometric amount provided that alcoholysis takes place between an alkoxy titanium, for example, butyl titanate (in other words, tetrabutoxy titanium) and a polyhydric alcohol.

As a matter of fact, when tetrafunctional tetrabutoxy titanium and pentaerythritol, a tetrafuctional polyol, are mixed at an equimolar ratio and are heated and reacted at 120° C., the polyol remains undissolved but a large amount of gel-like swollen precipitate occurs as a reaction product around the polyol. When the reaction is continued, the amount of liquid tetrabutoxy titanium decreases gradually. When heated over a long period of time, the reflux of butanol as one of reaction products, begins and butanol is hence distilled.

According to the finding of the present inventor, butanol is additionally formed from the precipitated remaining solid matter when the solid product is heated to 120°-180° C. subsequent to the removal of butanol by distillation. It has also been found that upon a heat treatment under reduced pressure, the solid matter is converted to a hardened porous product having a relatively high hardness and butanol is formed in a amount corresponding to butyl titanate employed.

In view of the above reaction process and reaction products, it may be contemplated that intermolecular alcoholysis is readily induced between the titanate and alcohol upon their heating and the subsequent heating, especially, the heat treatment under reduced pressure results in the formation of a polyol polytitanate which is linear and is presumably crosslinked to a high degree although details of its three-dimensional stereoscopic structure have not been fully elucidated.

The present inventor has also found that the thus-obtained solid product has catalytic effects to esterification reactions and/or ester interchange reactions as expected and can also lower the acid value of the reaction product significantly, leading to completion of the present invention.

The above esterification and/or ester interchange catalyst of the present invention is prepared by reacting an alkoxy titanium with a polyol and then subjecting the reaction product to a dealcoholization treatment to convert it into a highly-crosslinked product as described above. Its preparation will hereinafter be described, starting from the kinds of materials usable in the reaction of the alkoxy titanium and polyol.

Alcoholysis is of course expected to proceed partially in the reaction between the alkoxy titanium and alcohol. When the alkoxy titanium is polyfunctional, i.e., trifunctional or tetrafunctional and the alcohol is polyhydric, the stereoscopic structure of the reaction product becomes three-dimensionally complex. Accordingly, the dealcoholization in the subsequent step is hardly believed to proceed readily.

It has however been found, contrary to the above prediction, that when the dealcoholization is forcedly carried out at an elevated temperature, especially, under reduced pressure, the dealcoholization is easily caused to occur within the solid product, thereby providing a highly-crosslinked product.

For the reasons mentioned above, there is no particular limitation imposed on the polyol and alkoxy titanium to be employed in the preparation of the above-described catalyst of this invention. For example, the following reactants may be employed.

<Polyols>

Bifunctional polyols such as ethylene glycol, 1,2-propanediol, 1,3- and 1,4-butanediols, polyethylene glycol and polypropylene glycol; and Polyhydric alcohols and polyhydric high-molecular alcohols such as glycerin, diglycerin, 1,2,6-hexanetriol, trimethylolpropane, trimethylolbutane, pentaerythritol, dipentaerythritol, sorbitol, sorbitan and saccharoses as well as cellulose and polyvinyl alcohol.

<Alkoxy titaniums>

Tetrafunctional tetraalkoxy titaniums such as tetrabutoxy titanium and its tetramer, tetraisopropyloxy titanium, tetraethoxy titanium and tetraoctyloxy titanium;

Alcohol solutions of titanium trichloride and titanium tetrachloride; and

Compounds which are generally called "orthotitanic esters" (for example, butyl titanate).

Although the reaction of the above two reactants may proceed by simply mixing and heating them, it is preferable to react them gradually by dissolving them in portions in a solvent, namely, to react some alkoxy groups of the alkoxy titanium with the polyol and then to heat the reaction mixture in two steps so as to form a polyol polytitanate by alcoholysis, and further to conduct dealcoholization sufficiently under heat and reduced pressure so that the reaction polyol polytitanate is crosslinked to a high degree.

In general, when butyl titanate is used, the first step can be brought to completion by heating a reaction mixture, which has been obtained by adding a polyol to butyl titanate and reacting them to each other and which contains butanol formed as a reaction product, at 60°–160° C. for about 4 hours. After topping the thus-formed butanol, the heating temperature is raised to 160°–180° C. and the occurring alcohol is removed. The reaction product is then heated at reduced pressure, preferably, at 10 mmHg or lower for further 2 hours. After removal of the resulting alcohol formed through the dealcoholization, the solid product is ground to provide the intended catalyst.

As described above, a polyol and an alkoxy titanium are employed in the process for the preparation of a catalyst of this invention. The proportions of the equivalent of the polyol (i.e., OH equivalent) and that of the alkoxy titanium (i.e., OR equivalent) give considerable influence to the activities of the catalyst formed.

The term "OH equivalent" as used herein means the product of the number of moles of the polyol and the number of OH groups contained per molecule of the polyol. Similarly, the term "OR equivalent" indicates the product of the number of moles of the alkoxy titanium and the number of OR groups contained per molecule of the alkoxy titanium. The proportions of the OH equivalent and the corresponding OR equivalent may therefore be represented in terms of the molar ratio of the polyol to the alkoxy titanium (polyol/alkoxy titanium). Assuming by way of example, that the polyol and alkoxy titanium are reacted at a molar ratio of [B]/[A]. And also that the polyol contains b×OH groups and the alkoxy titanium has a×OR groups, the OH equivalent and OR equivalent are [B]×b and [A]×a respectively.

It is possible to enhance the activities of a catalyst by controlling the ratio of the alkoxy equivalent of its starting alkoxy titanium to the OH equivalent of the corresponding polyol. The ratio of OH equivalent to OR equivalent (OH equivalent/OR equivalent) may preferably be 1.8–0.9 (i.e., 1.8/1 –0.9/1). To achieve the above-mentioned preferred ratio, it is necessary to react the polyol and alkoxy titanium at a molar ratio (polyol/alkoxy titanium) in a range of (0.9–1.8)×a/b in which a is the number of alkoxy groups per molecule of the alkoxy titanium and b is the number of OH groups per molecule of the polyol. Excess OH equivalents are not suitable.

When a solid catalyst is prepared at a high OH equivalent, in other words, by using a polyol in a large proportion, there is a chance that the polyol may be dissolved out from the catalyst when the catalyst is applied to an esterification reaction. As a result, the polyol intervenes in the esterification reaction so that esters with the polyol incorporated therein (mixed esters, polyesters) occur as byproducts. It is hence not desirable to use the polyol in such an excess amount.

Use of a polyol in a high proportion may also lead to the formation of an oligomer derived from the corresponding titanium compound upon preparation of a catalyst. This oligomer is dissolved in the product of an esterification reaction, thereby increasing the acid value of the product. Excess OH equivalents are hence not desirable.

The catalytic activities of the catalyst can be enhanced by controlling the OH equivalent of the polyol and that of the alkoxy titanium as mentioned above. As an alternative, this can also be achieved by subjecting the resulting highly-crosslinked solid catalyst to a water treatment. This method is also effective although the degree of its effectiveness varies depending on the composition of each catalyst and preparation conditions therefor.

As a preferred method for enhancing the activities of a catalyst in the present invention, it may be mentioned to react a polyol and its corresponding alkoxy titanium at an OH equivalent/alkoxy equivalent ratio of about 1.5l–0.9/1 to conduct alcoholysis and dealcoholization sufficiently, thereby obtaining a crosslinked high-molecular product, and as a post treatment, to allow the high-molecular product to stand at room temperature or to heat the high-molecular product in butanol with water contained therein, whereby unreacted titanium-bound alkoxy groups still remaining on the surface of the solid mass of the polyol polytitanate are hydrolyzed into OH groups. Namely, the titanium-bound OR groups are converted to OH groups by hydrolysis owing to this activation treatment with water. The polyol polytitanate can hence have the polyol polytitanic acid structure, thereby allowing the polyol polytitanate to serve as a catalytically-effective component. If $Ti(OH)_4$ or an oligomer is derived from the titanium compound in the above-described activation treatment with water, the resulting catalyst can show improved catalytic activities in an intended dehydration and esterification reaction but develops such a problem that the acid value of the product of the esterification reaction or ester interchange reaction cannot be lowered. Its advantages as a catalyst are hence reduced substantially. Accordingly, care must be taken in this connection.

The principal feature of the solid catalyst of this invention resides in its selectivity for acids subjected to esterification reactions. Use of an alkoxy titanium having a larger steric volume compared with butoxy titanium such as benzyloxy titanium, 2-ethylhexyloxy titanium or cyclohexyloxy titanium involves a demerit that upon preparation of the catalyst, the conversion of the reaction product into a high-molecular product by dealcoholization proceeds slowly and many alkoxy groups tend to remain. A high reaction velocity is however expected in an esterification reaction of a bulky aryl carboxylic acid such as phthalic acid, benzoic acid or terephthalic acid so long as dealcoholization is allowed to proceed to a sufficient extent. When a polyol titanate is prepared, for example, from an alkoxy titanium of normal butanol or a lower alcohol and its activities are enhanced by a water treatment, the esterification velocity is very fast in the case of adipic acid which is a linear or straight-chain acid but is still insufficient in the case of phthalic acid. In the case of a catalyst prepared from tetra-2-ethylhexyloxy titanium on the other hand, its porosity is high and its activities are very high so that the reaction product can be treated to a low acid value in a short period of time. Titanium compounds of these higher alcohols can be prepared by adding an equivalent excess amount of a higher alcohol to butoxy titanium or isopropoxy titanium, which is an alkoxy titanium of a lower alcohol, and then simply heating the resultant mixture to conduct alcoholysis.

The present invention relates to a process in which a polyfunctional polyol is reacted with an alkoxy titanium to form, through alcoholysis and dealcoholization, a sufficiently-crosslinked high-molecular solid product which has the polyol polytitanate skeleton and is useful as a catalyst. This invention has therefore provided a technique that can afford an ester of a low acid value as a reaction product without undergoing a reaction with a monohydric alcohol and hence forming a soluble titanium alkoxide in the esterification reaction and the post treatment step can hence be either omitted or simplified by removing the solid catalyst through filtration or the like.

In esterification reactions making use of these solid catalysts having the polyol polytitanate skeleton, the acids can be esterified to a conversion of 99.9% in time periods as short as 3-4 hours.

The above solid catalysts of this invention have the highly-crosslinked high-molecular polyol polythetitanate skeleton as mentioned above. A further description will next be made of this feature.

When an alkoxy titanium containing bulky alcohol residues having a large steric volume such as 2-ethylhexyloxy groups is reacted with a polyol and the reaction product is then converted through dealcoholization into a highly-crosslinked high-molecular product, the product is soluble to solvents when the velocity of the dealcoholization is slow and the crosslinking is not achieved to a sufficient degree. As the alcohol residues of the alkoxy titanium are derived from a higher alcohol having a higher boiling point, the product becomes more soluble to solvents, for example, is soluble under heat in a solvent such as octanol.

If the insufficiently-crosslinked octanol-soluble portion and the highly-crosslinked octanol-insoluble are separated and are then independently treated with stirring at 80° C. in water-saturated butanol for 1 hour, namely, subjected to an activation treatment, both portions provide solid products which are both insoluble in octanol or have low solubility in octanol.

Comparing the activities of these solid products in esterification reactions for the preparation of phthalic acid esters, the catalyst obtained from the fully-crosslinked insoluble portion has very high activities and bring about high reaction velocities. On the other hand, the catalyst resulted from the insufficiently-crosslinked soluble portion has low activities apparently. This indicates that a highly-crosslinked titanium polymer having the polyol polytitanic acid skeleton shows higher activities.

When a catalyst is prepared by reacting a polyol with an alkoxy titanium having lower alcohol residues such as isopropyloxy groups, the dealcoholization proceeds at a relatively high velocity and facilitates the conversion of the reaction product into a highly-crosslinked high-molecular product. In order to lower the proportion of the solvent-soluble portion, it is however necessary to increase the temperature, time and degree of depression in the dealcoholization reaction. The catalytic activities are significantly reduced when the dealcoholization is insufficient.

As already mentioned above, U.S. Pat. No. 2,643,262 discloses titanium compounds which are similar to the titanium-base solid catalysts of this invention and contain chelate bonds formed from orthotitanic acid esters and certain specific glycols. Such titanium compounds may be considered as a sort of insufficiently-crosslinked polyol polytitanates.

The present Invention is characterized in that a reaction product is converted into a highly-crosslinked high-molecular product through a dealcoholization reaction and not only a bifunctional alcohol but also a polyfunctional alcohol are used as alcohols to increase the crosslinking degree so as to prepare a solid catalyst which is insoluble and highly-active in esterification reactions.

The above solid catalysts of this invention may each be prepared, for example, by adsorbing a polyol on one of various carriers such as silica, zeolite and molecular sieves and treating the polyol-bearing carrier with an alkoxy titanium so as to provide a composite matrix type catalyst with the carrier enclosed therein. Low-solubility catalysts can be prepared even from diols having particularly low functionality.

Needless to say, the above-described process may be effected in the opposite order, namely, the alkoxy titanium is adsorbed on one of various carriers, followed by its treatment with the polyol.

(Highly-crosslinked high-molecular polytitanic acids)

A further investigation was effected as to the above-described polyol polytitanate catalysts and polyol polytitanic acid catalysts. From the conception that as a polyol to be reacted with an alkoxy titanium, water may be considered as a bifunctional diol, the present inventor conducted a study on the reactions between alkoxy titaniums and water. As a result, it has been found that the above reactions can also provide useful titanium-base solid catalysts.

Namely, the present inventor proceeded with research in accordance with a prediction that a useful material having catalytic activities could also be obtained when water is reacted instead of a polyol subsequent to the provision of a useful solid catalyst of polyol polytitanate or polyol polytitanic acid through the reaction between an alkoxy titanate and a polyfunctional polyol as described above.

Unlike the reaction between an alkoxy titanium and a polyfunctional polyol, water does not always act as a bifunctional alcohol. When 1 mole of an alkoxy titanium is reacted with an excess amount, for example, 4 moles of water, the water is caused to act as monohydric alcohol so that an insoluble hydroxide corresponding to Ti(OH)$_4$ is formed. In other words, even if one wants to have water act as a dihydric alcohol on an alkoxy titanium with a view toward providing a high-molecular product, it is not absolutely easy to control the molecular weight of the resultant product since an alkoxy titanium containing either three or four alkoxy groups per molecule is employed. It is particularly important to note that in the course of conversion of the reaction product into a high-molecular product, oligomers are formed as the molecular weight of the high-molecular product is distributed. When these oligomers are hydrolyzed by adding excess water thereto in an activation treatment which will be described herein, the hydrolysis may proceed too much so that they are converted into Ti(OH)$_4$ or those susceptible to dissolution in an esterification reaction to which the catalytic effects of the catalyst is applied. It has hence been found that the acid value of the product of the esterification reaction cannot be lowered due to inclusion of such hydrolysates.

With the foregoing in view, the present inventor proceeded with a further investigation with a view toward developing a synthetic process which can minimize the formation of oligomers in the reaction between an alkoxy titanium and water. The present inventor thought that such a process would provide a catalyst which shows sufficient catalytic activities in an esterification reaction and can hence provide an ester of a low acid value at the end of the esterification reaction.

The above-mentioned way of thinking can be schematically described by the following reaction scheme.

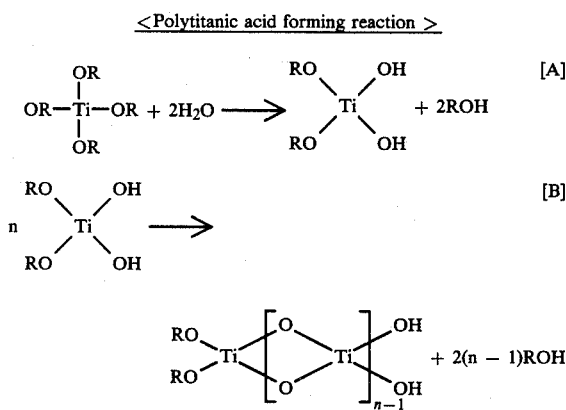

As shown by the above reaction scheme, 1 mole of the alkoxy titanium has an alkoxy equivalent of 4. When 2 moles of water are reacted with 1 mole of the alkoxy titanium, in other words, water in an amount equivalent to an OH equivalent of 4 is reacted (alkoxy equivalent/OH equivalent=1/1), a compound having the structure [A] is formed first of all and as a result of dealcoholization of the reaction product [A], a polytitanic acid having partially an ester structure of the structure [B] is then formed. For the sake of convenience, this reaction will hereinafter be called "polytitanic acid forming reaction". This polytitanic acid forming reaction proceeds through dealcoholization. The reaction can be accelerated by heating the reaction product [A] in a solid form or in a solvent or the resulting alcohol. Especially, by heating the reaction product [A] under reduced pressure while removing the resulting alcohol, the product [B] of the polytitanic acid forming reaction can be converted into a highly-crosslinked high-molecular product.

For the reasons mentioned above, it is extremely important to convert the product [B] into a high-molecular product in the polytitanic acid forming reaction while controlling the formation of oligomers as little as possible. Less oligomers are formed as the molecular weight of the product [B] increases. When a process is employed to react an alkoxy titanium with a large amount of water in one step, a monomer represented by Ti(OH)$_4$ is formed in a large amount or oligomer hydrates soluble in an esterification reaction mixture are formed. It is hence not desirable to use such a one-step process. If a high-molecular polytitanic acid [B] cannot be formed uniformly through the reaction of an alkoxy titanium and water upon preparation of a titanium-base solid catalyst by the polytitanic acid forming reaction, the above-described monomer or oligomer hydrates are byproduced in large amounts and as a result, the acid value of the resultant ester cannot be lowered. It is thus an important point how to obtain a high-molecular polytitanic acid (i.e., the above-described compound [B]) in a polytitanic acid forming reaction. The present invention has provided a solution to this subject.

In brief, the present invention relates to a process for the preparation of a polytitanic acid useful as a catalyst in esterification reactions and/or ester interchange reactions. The above polytitanic acid can be prepared by reacting an alkoxy titanium with water, followed by conversion of the reaction product into a highly-crosslinked high-molecular product. This invention also relates to a process for the preparation of a polytitanic acid useful as an esterification catalyst and/or ester interchange catalyst by activating a polytitanic acid, which has been prepared in the above-described manner and has an ester structure partly, through its water treatment.

The present invention will hereinafter be described in more detail.

Upon formation of the compound [A] in the abovedescribed polytitanic acid forming reaction, additional reactions also take place parallelly involving two or more molecules of the titanium compound. As a result, the dimerization and polymerization reactions of the alkoxy titanium occur as indicated by the next formula. These reactions proceed simultaneously along with the formation of the compound [A].

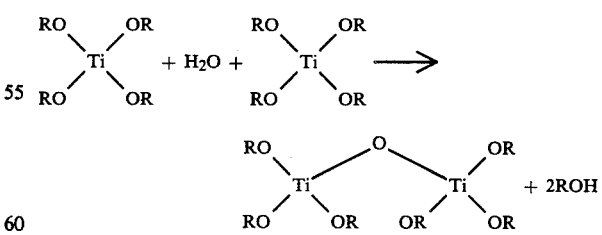

Turning next to the molar ratio of water to the tetraalkoxy titanium to be used in the above reaction, the dimer is formed when ½ mole of water is reacted to 1 mole of the tetraalkoxy titanium and an oligomer is formed when ½-1 mole of water is reacted to 1 mole of the tetraalkyloxy titanium. When 2 moles of water is reacted to 1 mole of the tetraalkoxy titanium, the abovedescribed reaction [A] or [B] is allowed to proceed provided that dealcoholization is caused to proceed completely, thereby forming a polytitanic acid which is a useful titanium-base solid catalyst.

Dimer, tetramers and still higher oligomers can be prepared by the reaction of the tetraalkoxy titanium and water as mentioned above, and the water may be reacted in an excess amount relative to the alkoxy equivalent where the alkoxy titanium is not contained in its monomeric form in the reaction product. When 1 mole of tetrabutoxy titanium tetramer (product of Tokyo Kasei Kogyo Co., Ltd.) is used by way of example, the alkoxy equivalent of the alkoxy titanium is 10. Even if water is used in an amount 1.5 times in terms of OH equivalent, valent, i.e., in an amount of 15 moles (i.e., a molar ratio of 15/1 relative to the tetramer), the reaction product is free of not only those derived from Ti(OH)$_4$ but also low-molecular titanium compounds, namely, oligomers soluble in the product of the esterification reaction. When the product of such a polytitanic acid forming reaction is used as an esterification catalyst, it contains many OH groups on the surface thereof and exhibits relatively high activities, whereby an ester having a low acid value is obtained.

However, the purification of the tetramer of an alkoxy titanium requires a considerable cost. Since similar effects can also be brought about even from the use of the alkoxy titanium in its monomeric form, it is not an essential requirement to use such a tetramer as a starting material.

When the hexadecamer of an alkoxy titanium is formed stepwise, i.e., by reacting 1 mole of the alkoxy titanium with ½ mole of water into the dimer, followed by a reaction with ¼ mole of water into the tetramer, followed further by a reaction with ⅛ mole of water into the octamer and followed still further by a reaction with 1/16 mole of water, water may be reacted little by little until the ratio of the OH equivalent of water to the OR equivalent of the alkoxy titanium reaches 1 eventually (in other words, until water is added to a total amount of 2 moles per mole of the alkoxy titanium). As a matter of fact, the objective can be attained by reacting the alkoxy titanium and water at a OR equivalent/OH equivalent ratio of 1/1 and then conducting the polytitanic acid forming reaction to a sufficient extent.

The solid [B] formed by the polytitanic acid forming reaction contains unreacted alkoxy groups at terminals. The conversion into the highly-crosslinked highmolecular product through the dealcoholization becomes more difficult to proceed, especially as the molecular weight and structural complexity of the solid [B] increases and as the alcohol, from which the alkoxy groups have been derived, becomes higher and bulkier. However, the dealcoholization can be achieved almost stoichiometrically by conducting it fully under reduced pressure. In general, the resultant catalyst has a heavier weight as unreacted alkoxy groups remain.

It is also an object of this invention to provide a process for modifying a highly-crosslinked solid-like highmolecular polytitanic acid, which has been prepared in the above-described manner, by its water treatment so as to enhance its catalytic activities. Namely, by hydrolyzing terminal alkoxy groups of the thus-prepared polytitanic acid with an excess amount of water, the alkoxy groups can be converted to OH groups so that more OH groups are formed on the surface of the solid catalyst and the catalytic activities can thus be enhanced. Here, water may be employed in an amount corresponding to the OH equivalent equal to the alkoxy equivalent up to an amount about twice the OH equivalent. If water is used too much, the hydrolysis is caused to proceed too much, resulting in formation of Ti(OH)$_4$ and oligomer hydrates which are less effective for esterification reactions.

Since the solid catalyst has been crosslinked to a high degree, its internal alkoxy groups are resistant to separation. It is hence possible to achieve the objective, namely, the enhancement of its activities to a sufficient extent by treating the solid catalyst with water in the same molar amount as the amount of water employed in the polytitanic acid forming reaction. As to its reaction with water, the objective of the reaction can be attained by heating it in a water-containing alcohol or allowing it to stand for a long period of time in a water-containing alcohol. As a result of this water treatment, the polytitanic acid (i.e., the solid catalyst) can contain many OH groups on its solid surface and its catalytic activities are hence enhanced.

In the present invention, the above-described polytitanic acid forming reaction can be carried out on a carrier. Since the use of a carrier renders the catalyst resistant to heat and facilitates the separation of the catalyst after an esterification or ester interchange reaction, it is preferable to conduct the polytitanic acid forming reaction in the presence of one of various porous carriers and fine powder.

As another merit which can also be brought about from the use of a carrier, may be mentioned that the composite matrix of the carrier and solid catalyst can minimize the dissolution of oligomers of titanic acid, in other words, their dissolution into the product of an esterification reaction. Illustrative examples of the carrier may include silica, alumina, zeolite, diatomaceous earth, molecular sieves, activated carbon, and so on.

In the above-described polytitanic acid forming reaction, the steric structure of the alkoxy groups in the titanium compound employed as a starting material gives considerable influence to the specificity of the catalytic activities. A tetraalkoxy titanium containing higher alcohol residues can be easily synthesized from a titanium compound containing lower alcohol residues. A low boiling-point alcohol is formed by adding 4 moles of a higher alcohol such as 2-ethyl hexanol, benzyl alcohol or cyclohexanol to 1 mole of a titanium compound containing lower alcohol residues such as butyl titanate or tetraisopropoxy titanium and then simply heating the resultant mixture under reflux. Four moles of a lower alcohol (butanol, isopropanol or the like) are formed when the reaction mixture is heated under reduced pressure until the reaction is brought to completion. Upon removal of the lower alcohol, a tetraalkoxy titanate containing residues of the higher alcohol is obtained. Using the thus-obtained tetra-2-ethylhexyloxy titanium (octyl titanate) as a starting material, water is added in such an amount that the ratio of OH equivalent/OR equivalent is 0.5/1 (namely, at a molar ratio of 1/1) under the assumption that the water acts as a diacidic base. Upon heating the resultant mixture, polytitanates are formed. The dimer however amounts to a majority of the polytitanates. The polytitanates are therefore substantially dissolved.

Upon an addition of additional water in an amount equal to an OH equivalent of 0.5 (i.e., 1 mole of water), partial crosslinking is caused to occur and a precipitate, which is the compound [A] in the above-described polytitanic acid forming reaction, is formed. When the polytitanic acid forming reaction is allowed to proceed sufficiently, the conversion of the reaction product into a high-molecular product proceeds at a low velocity but dealcoholization of 2-ethylhexyl alcohol takes place, thereby obtaining a porous solid catalyst which contains voids in the resultant solid product. The solid catalyst prepared in the above manner shows specificity in catalytic activities compared with a solid catalyst prepared from butyl or isopropyl titanate. For example, whereas the latter catalyst can achieve a high reaction velocity in the esterification of adipic acid but is unable to achieve any sufficient reaction velocity in the esterification of phthalic acid, the former solid catalyst prepared from octyl phthalate exhibits excellent high activities in esterification reactions of both acids.

As a reason for the above-described difference, it may be contemplated that esterification reactions are fast in the case of adipic acid but slow in the case of phthalic acid when the sizes of voids in a solid catalyst are small and the enlargement of such voids facilitates the adsorption of molecules of phthalic acid and can hence provide a solid catalyst having high activities. It is hence important to use a higher alkoxy titanium in the polytitanic acid forming reaction in order to prepare a solid catalyst with high activities.

The preparation process of the above solid polytitanic acid catalyst of this invention will hereinafter be described in further detail.

When a stoichiometric amount of water-containing butanol is added little by little to tetrabutyl titanate in the above-described polytitanic acid forming reaction, cloud occurs immediately after the addition but it disappears soon by its dissolution in an initial stage of the addition. As the amount of water increases, the reaction product changes from an oily substance to a colorless precipitate. The formation rate of the precipitate varies depending on the temperature and the rate of addition of water-containing butanol. As the alkoxy groups becomes higher, the formation of the precipitate becomes slower so that the reaction product is in an oily form. In the case of the tetramer of butyl titanate, it becomes solid at a relatively earlier stage but an oily precipitate is also observed. When excess water is incorporated in tetrabutoxy titanium, a solid precipitate composed principally of $Ti(OH)_4$ is obtained promptly. When the water-added reaction mixture is left over as is or is heated under reflux in butanol or a still higher alcohol, the alkoxy titanium is converted substantially in its entirety into a polytitanic acid while forming an alcohol. When butanol formed by using butoxy titanium as a starting material is distilled and is then quantitatively analyzed, butanol is obtained approximately in the stoichiometric amount including butanol added after the addition of water and that formed from the titanium compound. In the case of a higher alcohol, the reaction mixture is distilled at a high temperature under reduced pressure so that the alcohol is recovered. Needless to say, the reaction time of the polytitanic acid forming reaction varies depending on the reaction temperature. It is preferred to remove a liquid alcohol by distillation after formation of a solid substance in the alcohol and then to heat the solid substance under reduced pressure so as to effect dealcoholization sufficiently. If the reaction mixture is concentrated before a solid substance is not formed sufficiently, an oily oligomer remains together with the solid substance. When heated at 160°–200° C. under reduced pressure, dealcoholization takes place from the oily substance and also from the solid matter. Accordingly, the oily substance is also converted to a solid product having voids. The solid product has been crosslinked to such a high degree that it can be easily ground to fine powder when it is taken out and ground. It has also been found that the alcohol evaporated from the interior and the solid product was converted into a high-molecular product.

A description will next be made of a general method for activation by a water treatment. It is achieved by heating under reflux for about 1 hour in butanol, isopropanol or the like in the same amount as the amount of the water employed in the polytitanic acid forming reaction and the resulting solution is heated under reflux for about 1 hour. The higher alcohol formed by hydrolysis from the solid polytitanic acid catalyst is soluble in butanol, isopropanol or the like. The thus-activated product is collected by filtration, washed with butanol or the like and then heated and dried under reduced pressure, thereby making it possible to use the product as a solid catalyst.

When the solid catalyst prepared in accordance with this invention and composed of a polytitanic acid is used in an esterification reaction, it appears in view of the theory of reaction rate that the adsorption of the alcohol is very fast but the adsorption of the acid is in the controlling step of the reaction velocity. Although the esterification reaction can hardly be considered to be a first-order reaction in the case of $Ti(OH)_4$ catalyst, the esterification reaction proceeds in proportion to the concentration of the acid in the case of the catalyst of this invention. The velocity of an esterification reaction can be approximately estimated from the rate of formation of water. After removal of the stoichiometric amount of water by its azeotropic distillation, an ester mixture having a low acid value of 0.1 or smaller is obtained in several hours to somewhat more than 10 hours in the case of a low-activity catalyst. An acid value is generally defined as the number of milligrams of KOH per gram. Expressing the acid value in terms of the number of milliliters of 1/20N KOH titrated per gram in the present specification, the number of moles of a dibasic acid still remaining in a reaction mixture can be calculated from the above definition provided that the reacting weight is known (i.e., the number of moles of the dibasic acid = acid value $\times 1/20000 \times$ reacting weight $\times \frac{1}{2}$). In the formation of octyl adipate, the reacting weight of 1 mole is 450 g. The mole number of the remaining adipic acid is $1.125 \times 10^{-2}$ mole at an acid value of 1 and $1.125 \times 10^{-3}$ at 0.1 The conversion of adipic acid is believed to reach $(1-1.125 \times 10^{-3}) \times 100 = 99.88\%$ in the esterification reaction. When such an esterification reaction is carried out by using a solid hydrate which has been obtained by adding tetrabutoxy titanium to an alcohol containing a great deal of water, collecting the resulting precipitate by filtration and then drying the same under reduced pressure and is considered to be $Ti(OH)_4$, the initial velocity of dehydration in the esterification reaction is relatively fast but the final acid value cannot be lowered. Namely, the acid value of the product of the esterification reaction cannot be lowered to 1 or smaller even if many hours are spent. As a reason for this, it is contemplated that the adsorption of each of the alcohol and acid on the catalyst controls the reaction velocity and the esterification hence becomes a multi-order reaction and as a result, the reaction velocity is significantly lowered and the acid value of the reaction product is not lowered when the concentration of the acid is low.

The activities of the solid polytitanic acid catalyst of this invention appear to be proportional with the number of OH groups on the solid catalyst. By using the solid catalyst of the highly-crosslinked high-molecular polytitanic acid obtained in accordance with this invention, the acid value of the product of an esterification reaction can be lowered gradually to 0.1 or less as the reaction time goes on. Even in the case of an esterification reaction requiring a long reaction time for achieving such a low acid value, the time required to reduce the acid value to 0.1 or lower can be shortened considerably by enhancing the activities of the catalyst through its water treatment. The acid value can be achieved in three hours. From the viewpoint of activities only, the above-described titanium hydrate [Ti(OH)$_4$] has sufficient activities as far as the initial dehydration velocity of an esterification reaction is concerned. The titanium hydrate is however accompanied by a drawback that when it is mixed in a catalyst or it remains as an oligomer, the lowest acid value which the product of an esterification reaction can have is increased correspondingly.

The polytitanic acid forming reaction in which 2 moles of water is reacted with 1 mole of a tetraalkoxy titanium can therefore be conducted, for example, by adding the water to the tetraalkoxy titanium at a low temperature and then gradually heating the resultant mixture to convert the reaction product into a high-molecular product, by adding water in portions and conducting dealcoholization at the end of the reaction, or by conducting the reaction in an aqueous system containing a small amount of water in order to achieve the crosslinking of the reaction product to a sufficient degree. The essential thing is to take a measure so as to minimize the formation of crystalline Ti(OH)$_4$.

As the titanium compound useful as a starting material for the polytitanic acid forming reaction in this invention, any titanium compounds available commercially as tetraalkoxy titaniums may be used irrespective of the kinds of their alkoxy groups. Their oligomers such as dimers and tetramers may also be used.

In the case of a titanium compound in which its alkoxy groups have been derived from a lower alcohol, the titanium compound may be reacted with a higher alcohol to prepare a titanium compound containing residues of the higher alcohol for use as a starting material. In the case of a titanium compound containing higher alcohol residues in particular, it may be converted to a solid catalyst having sufficient activities for many acids when it is reacted with ¼ mole of water to form a solution of a polytitanate, followed by a further reaction with water in an amount corresponding to the same OH equivalent so as to subject the resulting solid and oily substances sufficiently to their polytitanic acid forming reactions; and the reaction products are thereafter treated with water to activate them. (Polyol polytitanic acids having the polytitanic acid structure)

The above-described two types of titanium-base solid catalysts are not absolutely free of problems. Especially, in the preparation reaction of the latter polytitanic acid, the solubility of the reaction product, i.e., polytitanic acid varies depending on the manner of addition of water and the proportion of water to be added. Depending on the levels of increased molecular weights and also on crosslinking degrees, some polytitanic acids may be partially dissolved in reaction systems when they are used as catalysts.

Even if they are used as solid catalysts with a view toward drawing their advantages fully, it is thus required to remove catalyst residue in some instances. It is therefore extremely important to apply a sufficient crosslinking treatment so as to convert them into insoluble solid catalysts.

The present inventor has conducted an extensive investigation as to the solubility of the above-described titanium-base solid catalysts. As a result, it has been found that the crosslinking treatment can be effectively achieved by making combined use of water, which may be considered as a bifunctional diol, and a polyfunctinal polyol.

It has hence been found as the third aspect of this invention that a solid titanium-base product, which has been prepared by reacting the reaction product of a tetraalkoxv titanium (orthotitanic acid ester) and a polyol or water with water or a polyol, converting the resulting product into a highly-crosslinked high-molecular product through its dealcoholization and then subjecting the highly-crosslinked high-molecular product to a water treatment to convert it into a hydrate thereof and contains in combination a (Ti—O—R'—O—Ti) structure (the skeletal structure of polyol polytitanic acids) derived from titanium and the polyol and a (Ti—O—Ti) structure (the skeletal structure of polytitanic acids) formed from titanium and water, is free from the problem of partial dissolution and is hence extremely useful as an esterification and/or ester interchange catalyst.

The third aspect of the present invention will hereinafter be described in detail.

The solid titanium-base catalyst according to the third aspect of this invention, which is composed of a polyol polytitanic acid containing the polytitanic acid structure, shows high activities as an esterification and/or ester interchange catalyst and permits extremely easy removal of catalyst residue. Its preparation process will next be described first of all.

When an alkoxy titanium, for example, a tetraalkoxy titanium (orthotitanic acid ester) is reacted with a polyfunctional alcohol (polyol) or water, a polyol polytitanate or polytitanic acid ester represented by the following formula [I] is formed in the first step of successive reactions.

$$(n + 1)RO-\underset{\underset{OR}{|}}{\overset{\overset{OR}{|}}{Ti}}-OR + (n + 1)HOR'OH \quad [I]$$

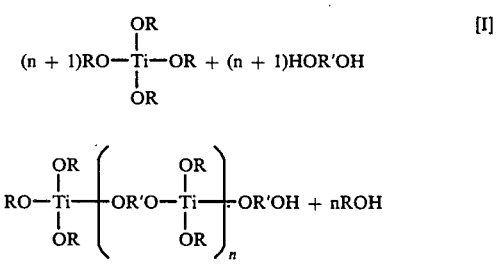

wherein R means a monohydric alcohol residue, R' in —OR'O— denotes a polyol residue, and when water is used, the moiety —OR'O— is changed to —O—.

As the molar ratio of the polyol or water to the alkoxy titanium is increased, in other words, the OH equivalent is increased in the above reaction, reactions are allowed to proceed between long-chain molecules and a crosslinking reaction proceeds in a step next to the stepwise reactions. When the cross-linking has proceeded, a product represented by the following formula

[II] is obtained. It remains as an insoluble precipitate even in organic compounds such as esters.

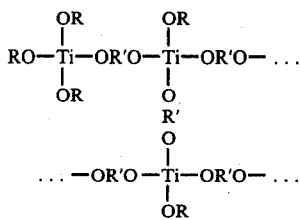

OR groups in a polyol polytitanate formed in the above-described manner are reacted with water or the polyol to form Ti—OH or Ti—OR'OH, which in turn reacts with its adjacent Ti—OR. Hence, the polyol polytitanate is converted into a solid product while forming (Ti—O—Ti) or (Ti—OR'O—Ti) bonds by dealcoholization. In this manner, there is obtained a polyol polytitanate having both (Ti—O—Ti) skeleton and (Ti—OR'O—Ti) skeleton, namely, the polytitanic acid structure in its molecule.

It has been empirically confirmed that the above dealcholoization proceeds almost stoichiometrically between the Ti—OR moiety of the alkoxy titanium and polyol or water. When this dealcoholization is allowed to proceed sufficiently by heating the reaction mixture under reduced pressure, it is observed that the liquid product changes into a solid product and in addition, an alcohol is released as bubbles from the solid reaction product. Namely, voids corresponding to the spatial volume of the released alcohol are formed inside the solid produced at the same time as the crosslinking reaction. Such dealcoholization has not been known in connection with other metal alcoholate compounds. It is a novel phenomenon which the present inventor has found for the first time.

The sizes of voids in the surface of the solid product and inside the solid product can be controlled by changing the kind of alcohol residues at the alkoxy sites of an alkoxy titanium employed as a starting material. This indicates that freedom of a certain degree can be enjoyed upon designing a solid catalyst. It is an extremely important feature. When dealcoholization is effected, for example, by using (sterically bulky) alcohol residues having a steric volume greater than the alcohol residues of the alkoxy titanium, the adsorption of a specific acid on the catalyst in an esterification reaction or ester interchange reaction can be facilitated and its catalytic activities can be enhanced.

Dealing further with this feature, a catalyst prepared from 2-ethylhexyl titanate may show higher activities in certain types of esterification reactions compared with a polyol polytitanic acid or polytitanic acid catalyst prepared from butyl titanate or isopropyl titanate. For example, the latter catalyst shows high activities in the case of adipic acid while the former catalyst exhibits higher activities in the case of phthalic acid or maleic acid. It has already been found from empirical results that the catalytic activities of these solid polyol polytitanate and polytitanic acid in esterification reactions allow the esterification reactions to proceed as first-order reactions corresponding substantially to the concentrations of the acids. The acids hence react and decrease linearly in proportion to the logarithms of the concentrations of the acids to form esters as the time passes on. In an esterification reaction, the adsorption of the acid on a solid catalyst is hence considered to control the velocity of the reaction. The velocity of adsorption of the acid is governed by the sizes of voids in a solid catalyst and the surface area of the solid catalyst. Corollary to this, a solid polytitanic acid or solid polyol polytitanate catalyst obtained by the removal of greater alkoxy groups shows broader selectivity to acids.

It is also an important feature of the third aspect of this invention that the above-described findings are effectively reflected upon preparation of catalysts.

Namely, it is also an important aspect of this invention to prepare a highly-crosslinked, ester-insoluble, high-activity catalyst by reacting an alkoxy titanium containing lower alcohol residues with a mixture of a monohydric alcohol having a greater spatial structure than the lower alcohol residues and a polyol to prepare a polyol titanate (note: this polyol titanate is different from polyol polytitanates as will be described subsequently herein), and then reacting the polyol titanate with water to convert it into a highly-crosslinked high-molecular product.

Needless to say, the use of the monohydric alcohol can be omitted provided that a monohydric alcohol having a large spatial structure is reacted in advance with an alkoxy titanium so as to use an alkoxy titanium containing alcohol residues of the large spatial structure.

As exemplary alkoxy titaniums useful in the preparation of polyol polytitanic acids, may be mentioned:

Tetrafunctional tetraalkoxy titaniums such as tetrabutoxy titanium and its tetramer, tetraisopropyloxy titanium, tetraethoxy titanium and tetraoctyloxy titanium;

Alcohol solutions of titanium trichloride and titanium tetrachloride; and

Compounds which are generally called "orthotitanic esters" (for example, butyl titanate).

On the other hand, the following compounds may be used as polyfunctional polyols:

Bifunctional polyols such as ethylene glycol, 1,2-propanediol, 1,3- and 1,4-butanediols, polyethylene glycol and polypropylene glycol; and Polyhydric alcohols and polyhydric high-molecular alcohols such as glycerin, diglycerin, 1,2,6-hexanetriol, trimethylolpropane, trimethylolbutane, pentaerythritol, dipentaerythritol, sorbitol, sorbitan and saccharoses as well as cellulose and polyvinyl alcohol.

Further, the following compounds may be used as monohydric alcohols:

$C_1$–$C_8$ lower alcohols, $C_4$–$C_8$ alcohols having still larger spatial structures such as t-butanol, 2-ethylhexanol, benzyl alcohol and cyclohexanol, and for improving the surface characteristics of solid catalysts, $C_9$–$C_{23}$ long-chain alcohols.

It is another significant feature of the present invention that catalytic characteristics can be modified by choosing a suitable kind of monohydric alcohol.

Namely, lower fatty acids provided for ester reactions or ester interchange reactions can be selectively adsorbed by using $C_1$–$C_8$ lower alcohols. By using bulky $C_4$–$C_8$ alcohols the spatial structures of which are greater than the lower alcohols, the porosity of solid catalysts can be increased. Further, $C_9$–$C_{23}$ long-chain alcohols are used to improve the surface characteristics of solid catalysts, for example, their wetting properties to oils.

These monohydric alcohols can achieve their objective when used in very small amounts. They are hence used by adding them in small amounts to polyfunctional polyols or alcohols.

The proportion of a polyol to its corresponding alkoxy titanium may be changed as desired. If the proportion of a polyol is decreased for example, the final product is a mixture of a polytitanic acid and a polyol polytitanic acid containing the polytitanic acid structure. If the proportion of the polyol is increased on the other hand, there is provided a solid catalyst which is principally composed of the polyol polytitanic acid structure and contains the polytitanic structure in a small proportion.

It is particularly preferable to use an alcohol having a large spatial structure, for example, 2-ethylhexanol or the like as a monohydric alcohol upon preparation of a polyol polytitanic acid, which contains the polytitanic acid structure partly, in accordance with the present invention. As an alternative, the monohydric alcohol having the large spatial structure may be omitted and instead, tetra(2-ethylhexyl) titanate is prepared beforehand, followed by its reaction with a polyol in an amount corresponding to ¼ of the alkoxy equivalent of the titanate and further by a reaction with water in the next step.

A description will next be made of a process in which a monohydric alcohol and polyol are used at a ratio of 3:1 in combination with an alkoxy titanium.

As their proportions suitable for the present invention, the alkoxy titanium, monohydric alcohol and polyol may be reacted at a ratio of 4:3:1 in terms of alkoxy equivalent, OH equivalent and OH equivalent respectively so that a polyol polytitanate is prepared. Thereafter, the monohydric alcohol titanate is reacted with water to convert it into a highly-crosslinked, high-molecular, solid catalyst.

A further description is now made taking trimethylolpropane as an example. When 3 moles of octanol and ⅓ mole of trimethylolpropane (⅓ mole because it is trifunctional) are used per mole of a tetraalkoxy titanium, the structure of the resulting polyol titanate may be expressed by the following formula [III]:

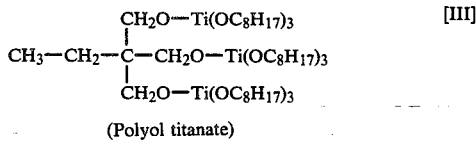

(Polyol titanate)

It is however impossible to actually synthesize the above compound [III] with a selectivity of 100%. The reaction product is a mixture of compounds in which two or more molecules of trimethylolpropane are coupled via titanium atoms.

Each terminal Ti—$OC_8H_{17}$ group of each molecule of the polyol titanate prepared in the above-described manner are reacted with its adjacent terminal Ti—$OC_8H_{17}$ group(s) or those contained in other molecules so that the polyol titanate is crosslinked to a higher molecular weight. The thus-crosslinked polyol titanate is obtained by the reaction with water, whereby it is subjected to dealcoholization and the terminal groups are changed to (Ti—O—Ti) bonds via Ti—OH groups. The polyol titanate is hence crosslinked further to a still higher molecular weight. This reaction route is the same as that described above in connection with polytitanic acids. In such a reaction as mentioned above, the polyol titanate is partially crosslinked and is rendered insoluble even when water is added at a molar ratio of ¼ relative to titanium in the titanium compound. However, the polymerization reaction becomes slower and more soluble components are contained in the final product as the alcohol becomes higher.

When reacting water with the above-described polyol titanate [III], it is preferred to allow the reaction to proceed stepwise. If water is added at once and the reaction is then conducted, 4 moles of water react with 1 mole of the titanium compound so that titanium hydroxide [Ti(OH)$_4$] is formed or insufficiently-crosslinked low-molecular oligomers of a titanic ester are byproduced. When the reaction product is used as a catalyst, its catalytic activities are insufficient. This catalyst has another problem as to its solubility, because the titanium component is dissolved out into the reaction system.

When a compound having a sufficiently high crosslinking degree is prepared by a stepwise reaction and is then crosslinked, dealcoholization takes place upon solidification of the crosslinked compound so that a solid catalyst containing many voids in the surface and interior thereof is produced. In order to increase the polymerization degree in the first step and to form sufficient voids in the solid substance in the second step so as to avoid separation of the soluble titanium compound even when used as a catalyst at elevated temperatures, it is preferred to react the compound with water in a stepwise fashion.

As to the amount of water to be used, 1.5–2.0 moles are preferred per mole of titanium of the abovedescribed polyol titanate. When a desired amount of water is reacted in two portions, a polyol polytitanate containing the polytitanic acid structure is formed and upon crosslinking the reaction product while subjecting same to dealcoholization, a solid product is obtained.

It is also possible to achieve a high crosslinking degree by increasing the proportion of the polyol to be used. To the tetraalkoxy titanium in an amount corresponding to an alkoxy equivalent of 4, the monohydric alcohol and polyol may be added in amounts corresponding to an OH equivalent of 2 or 1 and an OH equivalent of remaining 2 of 3 respectively. As more polyol is used, the solubility of the resulting polyol polytitanate become lower to solvents, in other words, structurally speaking, a solid polytitanic acid containing the polyol polytitanic acid structure at a higher ratio relative to the polytitanic acid structure is obtained. The reaction product tends to become an insoluble solid product from a relatively earlier stage of the preparation of the catalyst. Although the uniformity of the catalyst is somewhat sacrificed, it is advantageous to use the polyol in a higher proportion when a solvent-insoluble solid catalyst is desired.

When water is reacted first with an alkoxy titanium as opposed to the above-described procedure, it is preferable to convert the alkoxy titanium in advance to an alkoxy titanium compound containing higher alcohol residues, for example, tetra-2-ethylhexyl titanate in view of the selectivity of a catalyst to be obtained. Namely, after converting the alkoxy titanium into tetra-2-ethylhexyl titanate of a higher molecular weight by using water in an amount corresponding to an OH equivalent of ¼ relative to the OH equivalent of the titanate, tetra-2-ethylhexyl titanate is reacted with a polyhydric alcohol in an amount corresponding to an OH equivalent of ¼. The reaction product is thereafter subjected to dealcoholization to remove 2-ethylhexyl alcohol, whereby a polyol polytitanate having the polytitanic acid structure is prepared. The thus-obtained reaction product is activated by a water treatment which will be described subsequently, namely, unreacted Ti—O—(2-ethylhexyl) groups still remaining at the terminals of molecules of the reaction product are treated with excess water so as to subject them to hydrolysis. The unreacted groups are hence converted to Ti—OH groups, thereby preparing a polyol polytitanic acid having high catalytic activities and the polytitanic acid structure.

A description will next be made of activation by a water treatment.

The above-prepared solid catalyst of this invention still contains many alkoxy groups at terminals of its molecules, including the inside of the catalyst structure. Its catalytic activities can be enhanced if these alkoxy groups are fully treated and hydrated with water so as to cover the surface of the solid catalyst with Ti-OH groups. For this purpose, the above-prepared solid catalyst is brought into contact at room temperature or an elevated temperature with an alcohol which contains excess water, whereby terminal alkoxy groups are converted to OH groups and a high-activity polyol polytitanic acid having the polytitanic acid structure is hence provided.

The titanium-base solid catalyst of this invention, which has been prepared in a such a manner as described above, is more organic in nature than titanium oxide owing to the incorporation of the polyol in titanic acid. When a higher alcohol of a high boiling point is used in part and is caused to remain in the solid catalyst, the surface characteristics of the solid catalyst are improved to extents proportional to the amount of the alcohol still remaining there. It is hence possible to prepare a titanium-base compound which is wettable readily by solvents and can thus adsorb alcohols promptly thereon and when a long-chain alcohol is used in a small amount, has water-repellency.

(Utility)

The above-described three types of titanium-base solid catalysts of this invention are useful as catalysts for various esterification reactions and ester interchange reactions such as:

Dehydration and esterification reactions between acids and alcohols (for example, esterification reactions between monobasic, dibasic and polybasic acids and monofunctional, bifunctional and polyfunctional polyols;

Polyester forming reactions in the concurrent presence of dibasic acids, diols and monohydric alcohols;

Dehydration and esterification reactions and ester interchange reactions, upon preparation of mixed esters such as polyol bisalkyl adipates;

Esterification reactions and ester interchange reactions of fatty acids; and

Esterification reactions and ester interchange reactions among dibasic acids, fatty acids and polyols, such as alkyd paints and modified polyester paints.

EMBODIMENTS OF THE INVENTION

This invention will be more fully described by way of the following examples, but this invention is not limited only thereto.

Examples 1 -15 relates to highly-crosslinked polyol polytitanates, while Examples 16 -23 are directed to highly-crosslinked high-molecular polytitanic acids. On the other hand, Examples 24-30 are concerned with polyol polytitanic acids containing the polytitanic acid structure.

(EXAMPLES ON HIGHLY-CROSSLINKED POLYOL POLYTITANATES)

EXAMPLE 1

Twenty-three grams of tetrabutoxy titanium were placed in a 300 ml eggplant type flask, followed by an addition of 9.2 g of pentaerythritol. The contents were heated to 120° C. over an oil bath. Two hours later, a solid substance containing a gel-like precipitate was obtained. The temperature of the oil bath was then raised to 180° C., at which the solid substance was continuously heated under reduced pressure. The heating was continued until the distillation of butanol was ceased, thereby obtaining 19 g of butanol (yield: 95% of the theoretical value). After heating the contents for additional an two hours, they were taken out of the flask and ground to obtain 13 g of fine yellowish powder.

The above-obtained catalyst will be abbreviated as "P-Ti".

In a three-neck flask, 146 g (1 mole) of adipic acid and 222 g (3 moles) of butanol were charged. Water was removed by azeotropic distillation. As a catalyst, 0.5 g of the above-prepared P-Ti was added and a reaction was carried out while observing the amount of water distilled. Within 5 hours, water was distilled to about one half of its stoichiometric amount. Within 18 hours, water was distilled to about its stoichiometric amount, i.e., 36 ml. The titer (acid value; expressed in terms of the number of millliters of a 1/20 N alkaline solution titrated per g of the sample) per gram of the sample was 5.25 upon an elapsed time of 21 hours after the reaction. The acid value dropped successively as the reaction continued. Forty-six hours later, it reached 0.06. The amount of the recovered catalyst was 0.53 g, in other words, the recovery rate of the catalyst was approximately 100%. The acid value of the remaining acid was 0.1, which corresponds to 0.09% under an assumption that the reaction weight was 350 g. An acid value of 0.06 indicates a remaining amount of 0.05%, and in other words, teaches that 99.95% of the acid was reacted.

COMPARATIVE EXPERIMENT

To a system composed of 146 g (1 mole) of adipic acid and 222 g (3 moles) of butanol, 0.3 g of tetrabutoxy titanium, a conventional dehydration and esterification catalyst, was added as a catalyst to conduct a dehydration and esterification reaction (Since the dehydration and esterification reaction stops at a higher acid value as the amount of Ti(OBu)$_4$ increases, the catalyst was used in an amount of 0.3 g in the present Comparative Example instead of the amount of catalyst, i.e., 0.5 g in Example 1.)

In this dehydration and esterification reaction, the reaction temperature was low reflecting the amount of the added butanol and the reaction velocity was thus slow. Within 5 hours, water was distilled to one half of its stoichiometric amount and within 30 hours, water was distilled to a total amount close to its stoichiometric amount, i.e., 36 ml. At that point, the acid value was 1.8. The reaction was allowed to proceed further and the acid value was measured. Although the acid value was found to be 0.7 upon an elapsed time of 60 hours and 0.6 upon an elapsed time of 80 hours, it did not drop to a desired low level. The acid value was expected to drop somehow to a low level if the amount of the catalyst was reduced. However, it was unable to lower the acid value to 0.1 unlike Example 1.

EXAMPLE 2

Ten grams of pentaerythritol were added together with 20 g of "Molecular Sieve 13×" in 20 ml of water. After dissolving pentaerythritol under heat, the resultant mixture was allowed to stand. Undissolved pentaerythritol was washed with warm water and the residue was dried under heat in a reduced-pressure drier, thereby obtaining 24.5 g of the carrier with pentaerythritol adsorbed thereon. Tetrabutoxy titanium was then added in an amount corresponding stoichiomet to the adsorbed pentaerythritol, i.e, in an amount of 11.5 g and the resultant mixture was heated to 120 -180° C. After removal of the resulting butanol under reduced pressure, 26.0 g of a solid substance was obtained.

There was accordingly obtained a catalyst with P-Ti fixed thereon in an amount of 30% based on the molecular sieve.

To a mixture of 146 g (1 mole) of adipic acid and 222 g (3 moles) of butanol, 1.7 g of the above-prepared catalyst which was fixed on the molecular sieve was added to conduct a dehydration and esterification reaction. As a result, water was distilled out to total amounts of about 18 ml upon an elapsed time of 3 hours and a half and 36 ml upon an elapsed time of 16 hours. At that point, the acid value of the resultant ester was 0.44. The reaction mixture was heated and stirred for further 34 hours. As a result, its acid dropped to 0.04. A solid catalyst was recovered by filtration and its weight was 1.5 g. Its recovery rate was 88% (1.5/1.7 ×100).

EXAMPLE 3

To 17 g of tetrabutoxy titanium, 13.2 g of polyvinyl alcohol powder (commercial product) having a molecular weight of 2,000 was added. The resultant mixture was heated to 120 -180° C. and resulting butanol was removed. The reaction mixture was then continuously heated under a reduced pressure of 10 mmHg at 180° C. for 2 hours to obtain 15 g of fine brownish powder. The weight of recovered butanol was 14 g, thereby indicating that the reaction proceeded almost stoichiometrically. This catalyst will be abbreviated as PVA-T.

Added together were 146 g (1 mole) of adipic acid, 148 g (2 moles) of butanol and 0.5 g of PVA-Ti to conduct a dehydration and esterification reaction It took somewhat shorter than 3 hours until 18 ml of water was distilled by azeotropic distillation. Distillation of water to its stoichiometric amount took 18 hours. The reaction temperature increased as butanol reacted, so that the reaction velocity was somewhat increased. While adding butanol little by little in portions sufficient for azeotropic distillation and maintaining the reaction temperature at about 200° C. (190°-205° C.) after an elapsed time of 15 hours, the reaction was continued. As a result, the acid value dropped to 0.13 upon an elapsed time of 22 hours and 0. 09 upon an elapsed time of 26 hours.

EXAMPLE 4

To a mixture of 146 g (1 mole) of adipic acid and 325 g (2.5 moles) of 2-ethylhexanol, 0.5 g of PVA-Ti was added to conduct a dehydration and esterification reaction. The reaction temperature was as high as 170°-180° C. and the reaction velocity was hence fast. Within one hour, water was distilled to one half of its stoichiometric amount, i.e., 18 ml. Within 6 hours, water was distilled substantially to its stoichimetric amount, i.e., 36 ml. The acid value was 0.12 five hours later, 0.04 ten hours later and 0.02 fourteen hours later.

EXAMPLE 5

To a mixture of 148 g (1 mole) of phthalic anhydride and 325 g (2.5 moles) of 2-ethylhexanol, 0.5 g of PVA-Ti was added to conduct a dehydration and esterification reaction. Within about one hour, water was distilled to 9 ml and within 5 hours, water was distilled to a total amount substantially equal to its stoichimetric amount, i.e., 18 ml. The acid value was 0.12 five hours later, 0.4 ten hours later and 0.09 fifteen hours later.

EXAMPLE 6

To a mixture of 292 g (2 moles) of adipic acid, 81 g (0.9 mole) of 1,4-butanediol, 81 g (0.9 mole) of 1,3-butanediol and 58 g (0.64 mole) of butanol, 0.53 g of PVA-Ti was added to conduct a dehydration and esterification reaction. (This Example is intended to prepare a polyester having an average molecular weight of 2100.)

The stoichiometric amount of dehydrated water is 81.4 g. Distillation of water to a total amount of 40 g took 1 hour. Within 18 hours, 81 ml of water was distilled. A fresh supply of butanol was added to maintain the temperature of the reaction mixture at 200 -205° C. and the reaction mixture was then heated with stirring. As a result, the acid value was 0.2 twenty hours later. ThereafCter, an ester interchange reaction was carried out for 3 hours at 180° C.–20 mmHg to remove butanol. At that time, the acid value was 0.15.

EXAMPLES 7-9

(Experiments for Improved Catalytic Activities)

It was attempted to improve the activities of a catalyst by varying the molar ratio of a polyol to its corresponding titanate.

EXAMPLE 7

Dissolved in 60 ml of butanol were 6 g (0.033 mole) of d-sorbitol and 17 g (0.05 mole) of tetrabutoxy titanium. After refluxing the resultant solution for 6 hours, butanol was removed by distillation. Thereafter, the residue was heated for 3 hours at a reduced pressure of 20 mmHg to remove butanol further The yield of the reaction product was 10.2 g, although its stoichiometric yield is 8.4 g. Hence, the removal of butanol from the catalyst was insufficient.

A dehydration and esterification reaction was conducted by adding 0.5 g of the above-prepared catalyst to a mixture of 146 g (1 mole) of adipic acid and 148 g (2 moles) of butanol. Distillation of 16 ml of water (about one half of its stoichiometric amount) took 2.5 hours. It was 14 hours later that the total amount of distilled water reached 36 ml (distillation of the stoichiometric amount). The acid value dropped to 2.0 fifteen hours later and to 0.10 thirty hours later.

EXAMPLE 8

In 10 ml of butanol, 7.2 g (0.039 mole) of d-sorbitol and 17 g (0.05 mole) of tetrabutoxy titanium were refluxed. Six hours later, a crosslinking reaction was carried out for 3 hours under reduced pressure. The yield of the reaction product was 10.6 g and the removal of butanol had not been achieved completely. A dehydration and esterification reaction was conducted by adding 0.5 g of the above catalyst to a mixture of 1 mole of adipic acid and 2 moles of butanol. Distillation of water took place to a total amount of 16 ml within 2 hours and to a total amount of 36 ml within 14 hours. Twenty-four hours later, the acid value was 0.08.

EXAMPLE 9

In 60 ml of butanol, 9 g (0.049 mole) of d-sorbitol and 17 g (0.05 mole) of tetrabutoxy titanium were refluxed. Six hours later, a crosslinking treatment was applied for 3 hours at 180° C. under reduced pressure. The yield of the reaction product was 12 g and in view of its stoichiometric yield of 11.6 g, the reaction product had been crosslinked almost stoichiometrically. About one third of its OH groups appeared to exist on the surface of the catalyst. A dehydration and esterification reaction was conducted by adding 0.5 g of the above catalyst to a mixture of 1 mole of adipic acid and 2 moles of butanol. Distillation of water took place to a total amount of 16 ml within 2 hours and to the stoichiometric amount of 36 ml within 8 hours. At that time, the acid value of the resultant ester was 1.0. Its acid value dropped to 0.2 twelve hours later and further to 0.08 sixteen hours later.

The above-described results of Examples 7-9 are summarized in Table 1.

TABLE 1

| Ex. | Amount of d-sorbitol used | Amount of tetrabutoxy titanium used | OH equivalent / OBu equivalent | Remarks (acid value) |
|---|---|---|---|---|
| 7 | 6 g (0.033 mole) (0.033 × 6) OH equivalent: 0.198* | 17 g (0.05 mole) (0.05 × 4) OBu equivalent: 0.2** | 1/1 | 2.00 (15 hrs. later) 0.10 (30 hrs. later) |
| 8 | 7.2 g (0.039 mole) (0.039 × 6) OH equivalent: 0.234* | 17 g (0.05 mole) (0.05 × 4) OBu equivalent: 0.2** | 1.2/1 | 0.08 (24 hrs. later) |
| 9 | 9 g (0.049 mole) (0.049 × 6) OH equivalent: 0.294* | 17 g (0.05 mole) (0.05 × 4) OBu equivalent: 0.2** | 1.5/1 | 0.20 (12 hrs. later) 0.08 (16 hrs. later) |

Note:
*The OH equivalent of 1 mole of d-sorbitol is 6.
**The OBu equivalent of 1 mole of tetrabutoxy titanium is 4.

EXAMPLE 10

Using 0.5 g of the sorbitol-polytitanate base catalyst prepared in Example 9, a dehydration and esterification reaction was conducted between 146 g (1 mole) of adipic acid and 32.5 g (2.5 moles) of 2-ethylhexanol. The catalytic activities were improved significantly. Water was distilled to one half of the stoichiometric amount, i.e., 18 ml within 40 minutes and substantially to the stoichiometric amount of 36 ml within 2 hours. At that time, the acid value was 3.71. When the reaction was continued further, the acid value dropped to 0.17 four hours later and further to 0.03 six hours later.

EXAMPLE 11

(Experiment for Improved Catalytic Activities)

An experiment was conducted to improve the activities of a catalyst by treating it with water.

The reaction product of the polyol and titanate (OH equivalent/OBu equivalent =1), which was employed in Example 7, was placed in water and stirred for 2 hours there. The product was collected by filtration, followed by its drying to prepare 0.5 g of a surface hydrate of the polyol polytitanate as a catalyst. In the same manner as in Example 10, an experiment was conducted by using the above-prepared catalyst to produce dioctyl adipate. The reaction velocity was substantially as high as that in Example 10. Namely, substantially the stoichiometric amount of water was distilled within 2 hours. The acid value dropped to 0.04 six hours later.

EXAMPLE 12

<Preparation of Mixed Ester (1)>

To 387 g (1.5 moles) dibutyl adipate, 74 g (0.5 mole) of phthalic anhydride was added, followed by an addition of 1,4-butanediol (0.5 mole). The resultant mixture was stirred at 125° C. Within 30 minutes after the addition of the diol, 95% of the phthalic anhydride was found to have reacted as a result of a quantitative analysis of the remaining phthalic anhydride by titration.

One hour later, 0.5 g of PVA-Ti (described in Example 3) was added. The stoichiometric amount, namely, 37 g (0.5 mole) of butanol was added and the reaction temperature was raised to 165°-185° C. to conduct a dehydration and esterification reaction while additionally supplying 30 g of butanol in portions as an extra supply for azeotropic distillation in the course of the reaction. After removal of water to its stoichiometric amount, the acid value was 1.2 thirteen hours later and 0.24 twenty hours later. Thereafter, an ester interchange reaction was conducted under reduced pressure, namely, 160°-185° C./200 mmHg–10 mmHg to recover butanol. At that time, the acid value was 0.23 ml/g. After washing the reaction product with water and then with an alkaline solution, excess dibutyl adipate was driven off under reduced pressure. As a residue, 164 g of 1,4-butanediol butyl adipate butyl phthalate was obtained. Its viscosity at 21° C. was 102.5 cps. As a result of an analysis by liquid chromatography, at least about one half of the reaction product was composed of 1,4-butanediol butyl adipate butyl phthalate [$C_4H_9OCO(CH_2)_4COO(CH_2)_4OCOC_6H_4$—$COOC_4H_9$]. The reaction product was a mixture of high-molecular esters including three types of high-molecular oligomers in addition to 1,4-butanediol butyl adipate butyl phthalate. When this reaction product is used as a plasticizer for polyvinyl chloride, it can impart substantially the same degree of flexibility to polyvinyl chloride at a concentration approximately equal to that of conventional DOP. On the other hand, its loss in weight on heating at 170° C. is about one third compared with DOP. Therefore, the heat resistance can be improved significantly.

From the above results, it is understood that the above-prepared mixed ester can be used as a plasticizer having excellent plasticity.

EXAMPLE 13

<Preparation of Mixed Ester (2)>

Dissolved in 30 ml of acetone was 10 g of trimethylolpropane, followed by an addition of 5 g of "Chromosorp W" (trade name; product of Gasukuro Kogyo Inc., Tokyo, Japan) as a carrier composed of diatomaceous earth and kaolin. The resultant mixture was left over to adsorb trimethylolpropane on the carrier. The acetone mixture was filtered to collect the carrier. The carrier was then washed with a small amount of acetone, followed by its drying under reduced pressure to prepare a trimethylolpropane adsorbed carrier.

The amount of the above-adsorbed trimethylolpropane was 0.5 g. To the trimethylolpropane adsorbed carrier, 80 g of a xylene solution containing 1.05 g of tetrabutoxy titanium was added and the resultant mixture was heated under reflux. One hour later, the solvent and resulting butanol were topped and the temperature of the residue was raised to 180° C., at which it was heated for 3 hours under reduced pressure, namely, at 20 mmHg, thereby removing the formed butanol completely. As a result, 5.7 g of a carrier-borne catalyst was prepared. To a mixture of 306.6 g (2.1 moles) of adipic acid, 63 g (0.7 mole) of 1,3-butanediol and 52 g (0.7 mole) of butanol, 1.5 g of the above-prepared catalyst was added. A dehydration and esterification reaction was conducted under azeotropic distillation. From the time point that water had been distilled to a total amount of 16 ml equivalent to 25% of its stoichiometric amount, a dehydration reaction was conducted while adding 207 g (2.8 moles) butanol. As a result, the acid value dropped to 1.0 sixteen hours later. From this acid value, the conversion was calculated to be about 98.5%. Twenty-four hours later, the acid value dropped to 0.20. The reaction product at that time point is considered to be a mixture of 0.7 mole of butyl 1,3-butane diol adipate and 1.4 moles of dibutyl adipate. After removal of unreacted butanol by treating the reaction mixture under slightly reduced pressure, the temperature was raised to 180° C., at which the resulting butanol was driven off under reduced pressure (to a final pressure of 20 mmHg). It was possible to obtain butanol in an amount substantially equal to its stoichiometric amount, thereby confirming that the ester interchange reaction is allowed to proceed fully by the above-prepared catalyst. By this ester interchange reaction, 0.7 mole of 1,3-butanediol bisbutyl adipate and 0.7 mole of dibutyl adipate are expected to occur. As a result of distillation under reduced pressure, 200 g (0.77 mole) of dibutyl adipate was however recovered actually. The acid value was 0.15 after the ester interchange reaction. By washing the reaction mixture with an aqueous alkaline solution subsequent to removal of the catalyst by filtration, it was possible with extreme ease to lower the acid value to a low level (0.03). The reaction product was separated by distillation. After removal of dibutyl adipate by distillation, the viscosity of the reaction product was 70 cps. The reaction product was a mixed ester which contained three types of oligomers including 1,3-butanediol bisbutyl adipate as a principal component. As a result of distillation, about 79% of the remaining liquid mixture (reaction product) was found to be 1,3-butanediol bisbutyl adipate having a high boiling point (228°-233° C./0.3 mmHg). This reaction product is usable as a plasticizer for polyvinyl chloride, which exhibits substantially the same level of plasticity as DOP when used in an amount of 95% of DOP. Its volatility is as little as about 10% of DOP's volatility. Namely, a polyvinyl chloride sheet making use of the reaction product as a plasticizer has such superb heat resistance that its hardness does not vary substantially when heated at 80° C. for 8 weeks and further at 100° C. for 2 weeks. In the case of DOP on the other hand, more than 30% of the plasticizer is lost by its evaporation in 7 weeks and the hardness increases to 95 or higher.

EXAMPLE 14

To 34 g (0.1 mole) of tetrabutoxy titanium, 52 g (0.4 mole) of 2-ethylhexanol was added. Over an oil bath, the resultant mixture was heated to 180 -190° C. at which the mixture was heated under reflux for 1 hour. The resulting butanol was distilled under normal pressure - reduced pressure (25 mmHg) so that 27.6 g (93%) of butanol was recovered along with tetraoctyloxy titanium. Thereafter, 13.6 g (0.1 mole) of pentaerythritol was added in such an amount that the ratio of the octyloxy equivalent of the tetraoctyloxy titanium to the OH equivalent of the pentaerythritol was 1/1. After heating the resultant mixture at 180°-190° C. for 2.5 hours, the reaction mixture was subjected to a heat treatment for 2 hours first under reduced pressure of 30 mmHg and then of 1 mmHg so that the resulting 2-ethylhexanol was distilled off and at the same time, pentaerythritol polytitanate was obtained as a solid substance. Then, 50 g of a butanol solution containing 10 g of water was added to the solid substance and the resulting mixture was stirred at 80° C. for 2 hours to subject the solid substance to an activation treatment. After suction filtration, the thus-collected solid substance was thoroughly washed with butanol and then dried under reduced pressure to obtain 24.6 g of a solid substance. In octanol, this solid substance was able to adsorb monooctyl phthalate at a rate of 0.117 mmole/g.

Using 0.5 mole of phthalic anhydride and 1.25 moles of 2-ethylhexanol, a dehydration and esterification reaction was conducted in the presence of 0.8 g of the above-prepared solid catalyst. Three hours later, later the acid value was 0.08. Three hours and a half, the acid value was found to be 0.05. Hence, an ester of a low acid value was obtained in a short period of time. The reaction mixture was filtered by using activated clay as a filter aid, thereby obtaining DOP in a colorless form.

Similarly, an esterification reaction was conducted at 160°-190° C. by using 0.5 moles of adipic acid and 1.25 moles of butanol in the presence of 0.8 g of the above-prepared solid catalyst while adding butanol in portions. The acid value dropped to 0.5 seven hours later and further to 0.03 ten hours and a half later. The reaction mixture was then filtered by using activated clay as a filter aid, thereby obtaining dibutyl adipate of an extremely low acid value.

Besides, another esterification reaction was conducted at 160°-190° C. by using 0.5 moles of phthalic anhydride and 1.25 moles of butanol in the presence of 0.8 g of the above-prepared solid catalyst while adding butanol in portions. The acid value dropped to 0.05 nineteen hours later. Although the selectivity for phthalic acid is still not considered to be sufficient in the above esterification reaction, the activities of the solid catalyst were improved to a level substantially equal to the activities of soluble titanium-base catalysts, whereby it was able to obtain esters of low acid values.

EXAMPLE 15

To 34 g (0.1 mole) of tetrabutoxy titanium, 52 g (0.4 mole) of 2-ethylhexanol was added. Over an oil bath, the resultant mixture was heated to 180°–190° C. at which the mixture was heated under reflux for 1 hour. The resulting butanol was distilled under normal pressure —reduced pressure (25 mmHg) so that 27.6 g (93%) of butanol was recovered along with tetraoctyloxy titanium. Thereafter, 1,4-butanediol was added in an amount of 18 g (0.2 mole) so that the ratio of the octyloxy equivalent of the tetraoctyloxy titanium to the OH equivalent of the 1,4-butanediol was 1/1. After heating the resultant mixture at 180°–190° C. for 2 hours, the resultant 2-ethylhexanol was distilled under reduced pressure of 30 mmHg to obtain a solid product.

Then, 45 g of 2-ethylhexanol was added. The resulting mixture was heated for 1 hour at 180°–190° C. over an oil bath. The dissolved portion was separated by hot decantation. The undissolved portion was added with 50 g of butanol and 10 g of water. After heating the resultant mixture at 80° C. for 1 hour with stirring, the reaction mixture was filtered and the thus-collected solid substance was washed with hot butanol. It was then dried under reduced pressure to obtain 10.5 g of a solid catalyst.

On the other hand, a solid substance which had been obtained by concentrating the 2-ethylhexanol solution under reduced pressure was heated with stirring at 80° C. for 1 hour in a mixed solution of 10 g of water and 50 g of butanol. The reaction mixture was then filtered and the thus-collected solid substance was washed with hot butanol. It was then dried under reduced pressure to obtain a solid catalyst of 11.5 g. To mixtures composed individually of 0.5 mole of phthalic anhydride and 1.1 moles of 2-ethylhexanol, the above-prepared solid catalysts were separately added in an amount of 0.8 g. In the presence of a small amount of toluene, a dehydration and esterification reaction was conducted at 190°–210° C. under azeotropic distillation. In the case of the former catalyst (the activated substance obtained from the undissolved portion), the acid value dropped to 0.10 two hours later, 0.06 three hours later and 0.04 four hours later. In the case of the latter catalyst on the other hand, the acid value was 0.30, 0.15 and 0.10 respectively. There was thus a significant difference in reaction velocity. Especially, the degree of drop in acid value after an elapsed time of 2 hours was extremely poor in the case of the latter catalyst. After the esterification reaction, a small amount of activated clay was added as a filter aid and the reaction mixture was then filtered. Remaining 2-ethylhexanol was distilled off under reduced pressure to obtain colorless DOP of a low acid value. Incidentally, the removal of catalyst residue was extremely easy. A sheet was produced by using the above-prepared DOP as a plasticizer for polyvinyl chloride without any further treatment or processing. In order to compare its properties with those obtained by using a commercial plasticizer, a 100° C.-1500 hour heating test was conducted. No differences were observed at all in their coloration. (Examples on Highly-Crosslinked High-Molecular Polytitanic Acids)

EXAMPLE 16

Dissolved in 70 g of butanol was 34 g (0.1 mole; OBu equivalent: 0.4) of tetrabutoxy titanium, followed by dropwise addition of 70 g of a butanol mixture, which contained 3.6 g (0.2 mole; OH equivalent: 0.4) of water, with stirring at room temperature. Simultaneously with the initial dropwise addition, the reaction mixture was clouded. However, the butanol mixture was dissolved completely when the dropwise addition of the butanol mixture was stopped. The butanol mixture was added over 1 hour. Upon completion of the the dropwise addition, an oily substance was formed as a precipitate. The reaction mixture was heated with stirring and under reflux. Four hours later, some solid product was precipitated. Upon distillation of butanol, there was obtained a residue a majority of which was composed of a solid precipitate. While carefully avoiding bumping, the residue was heated under reduced pressure so that butanol was distilled. The residue was finally heated for 3 hours at 180°–190° C./20 mmHg. It was confirmed that butanol was no longer distilled. Thereafter, the resultant product was heated for further 15 minutes at 1 mmHg.

A solution of 3.6 g of water in 20 g of butanol was then added. After heating the resulting mixture for 1 hour, the resultant precipitate was collected by filtration. The precipitate was washed with butanol and then dried under reduced pressure, thereby obtaining 8.4 g of a solid polytitanic acid catalyst.

To a mixture of 146 g (1 mole) of adipic acid and 325 g (2.5 moles) of 2-ethylhexanol, 0.5030 g of the above-prepared solid polytitanic acid catalyst was added. A dehydration and esterification reaction was then conducted at 180°–200° C. in the presence of a small amount of toluene. Within 30 minutes, water was distilled to one half of its stoichiometric amount. Eighty minutes later, the distillation of water ceased substantially. The acid value was 0.13 upon an elapsed time of 120 minutes and 0.24 upon an elapsed time of 240 minutes.

<Comparative Example>

Dissolved in 5 g of butanol was 3.4 g of tetrabutoxy titanium. The resultant solution was added under reflux to a mixture of 20 ml of water and 50 ml of butanol. A colorless precipitate was crystallized out. Six hours later, the precipitate was collected by filtration and then washed. The precipitate was then allowed to stand overnight at 80° C. in a reduced-pressure drier. Calculating the reaction product as $Ti(OH)_4$, 0.7005 g of the reaction product was used as an amount corresponding to 0.5 g of the polytitanic acid in Example 16. Thus, 0.7005 g of the reaction product was added to a mixture of 146 g (1 mole) of adipic acid and 325 g (2.5 moles) of 2-ethylhexanol so as to conduct a dehydration and esterification reaction. In the dehydration and esterification reaction, distillation of water took place quickly. One half of its stoichiometric amount was distilled within 45 minutes and nearly the stoichiometric amount of water was distilled within 90 minutes. The acid value of the reaction product was measured. It was however 6.6 ml/g three hours later, 4.1 seven hours later and 2.2 fifteen hours later. The acid value did not drop below 1 even when the reaction product was heated for many hours. The velocity of formation of water by the dehydration and esterification reaction appeared to increase if the surface of the solid catalyst was hydrated. It was however found contrary to the above prediction that such a hydrated catalyst was unable to lower the acid value of the reaction product of an esterification reaction.

EXAMPLE 17

To a solution of 9.7 g of tetrabutoxy titanium tetramer [Ti$_4$O$_3$(OBu)$_{10}$; product of Tokyo Kasei Kogyo Co., Ltd.], was added with heating a solution of 1.35 g (0.075 mole; OH equivalent: 0.15) of water in 20 g of butanol. They were reacted in the same manner as in Example 16. The OBu equivalent of tetrabutoxy titanium tetramer is 10 per mole. Therefore, 9.7 g of tetrabutoxy titanium tetramer is equivalent to 0.01 mole and the OBu equivalent of 9.7 g of tetrabutoxy titanium tetramer is 0.1 (0.01×10=0.1). The final reaction product appears to be a polytitanic acid represented by the following structural recurring unit:

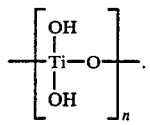

Following the procedure of Example 16, 0.5005 g of the above-prepared catalyst was added to a mixture of 146 g (1 mole) of adipic acid and 325 g (2.5 moles) of 2-ethylhexanol and in the presence of a small amount of toluene, a dehydration and esterification reaction was carried out at 180°-220° C. Within 20 minutes, water was distilled to one half of its stoichiometric amount. The stoichiometric amount of water was dissolved within 2 hours. Four hours later, the acid value was already 0.05. It dropped to 0.02 five hours later.

EXAMPLES 18 & 19

Seventeen grams of butyl titanate (0.05 mole; OBu equivalent: 0.2) was taken up in 10 g of butanol and while adding a mixture of 1.8 g (0.1 mole; OH equivalent: 0.2) of water and 20 g of butanol little by little, the resulting mixture was heated to 100°-120° C. at which they were reacted for 1 hour. In this reaction, an oily substance was formed at the beginning and a solid product was crystallized out subsequently. After heating the reaction mixture for a further 3 hours, the resulting butanol was removed by distillation and the residue was heated at 180°-190° C. for 3 hours under reduced pressure and then for an additional 15 minutes at 1 mmHg. The reaction product was left over in the mixed solvent which consisted of 0.80 g (OH equivalent: 0.088) of water and 20 g of butanol. The mixture was then heated for 1 hour and the solvents and resultant butanol were completely distilled out under reduced pressure, thereby obtaining 5.2 g of a solid catalyst.

To a mixture of 146 g (1 mole) of adipic acid and 325 g (2.5 moles) of 2-ethylhexanol, 0.5007 g of the above-prepared solid catalyst was added and in the presence of a small amount of toluene, a dehydration and esterification reaction was conducted at 180°-200° C. As a result, water was distilled to one half of its stoichimetric amount within 35 minutes and to the stoichiometric amount within 105 minutes. The acid value of the product of the esterification reaction was 0.08 two hours later, 0.04 three hours later and 0.03 four hours later.

To a mixture of 148 g (1 mole) of phthalic acid and 325 g (2.5 moles) 2-ethylhexanol, 0.5010 g of the same solid catalyst was added and in the presence of a small amount of toluene, a dehydration and esterification reaction was conducted at 180°-205° C. Water was distilled to one half of its stoichiometric amount within 40 minutes and to the stoichiometric amount within 4 hours. The acid value was 3.35 at that time. The acid value dropped to 0.15 eight hours later and further to 0.02 twelve hours later.

In both esterification reactions, the above-prepared catalyst was able to provide low acid values as described above. It is however appreciated that the velocity of esterification varies considerably depending on the type of each acid.

EXAMPLE 20

When 52 g (0.4 mole) of 2-ethylhexanol was added to 28.4 g (0.1 mole; isopropyl equivalent: 0.4) and the resultant mixture was heated to 160°-180° C., isopropanol was distilled about 30 minutes later. The reaction mixture was finally heated at 180° C./20 mmHg to obtain approximately the stoichiometric amount (23 g) of isopropanol. The liquid residue was considered to be tetra-2-ethylhexyloxy titanium in a liquid form. While chilling the liquid residue, an isopropanol solution containing 1.8020 g (0.1 mole; OH equivalent: 0.2) of water was added at a low temperature. The reaction mixture was then heated to dissolve some cloud which had occurred, thereby forming oligomers of the titanic acid ester. Under chilling again, the remaining portion, i.e., 1.7961 g (0.1 mole; OH equivalent: 0.2) of water was added as a solution in isopropanol. The temperature of the resultant mixture was raised with stirring. At about 80° C., crystallization of a colorless precipitate started to provide a cloudy solution. After heating the cloudy solution under reflux, isopropanol was distilled out and under reduced pressure, volatile components were also removed to obtain an oily substance having a high viscosity and containing solids. The oily substance was then heated at 180° C. under reduced pressure so as to solidify the same. The resultant solid substance was again taken up in 2-ethylhexanol, followed by heating at 180°-190° C. for 8 hours. Thereafter, the resultant mixture was again heated under reduced pressure for 30 minutes to concentrate the same. The residue was then added to 50 g of butanol which contained 3.6 g of water. The thus-prepared mixture was treated with stirring at 130° C. for 20 minutes. The resulting precipitate was collected by filtration, followed by its drying under reduced pressure to obtain 8.6 g of a solid catalyst. This yield was very close to the stoichiometric yield of TiO$_2$.

To a mixture of 148 g (1 mole) of phthalic anhydride and 325 g (2.5 moles) of octanol, 0.5030 g of the above-prepared solid catalyst was then added to conduct a dehydration and esterification reaction. Water was distilled to about one half of its stoichiometric amount within 30 minutes and approximately to the stoichiometric amount within 70 minutes. The acid value of the product of the esterification reaction was found to be 0.14 ninety minutes later, 0.08 two hours later and 0.04 four hours later.

EXAMPLE 21

Added to 34 g (0.1 mole; OBu equivalent: 0.4) of butyl titanate was 26 g (0.2 mole) of 2-ethylhexanol. The resultant mixture was heated to 160°-180° C., at which the contents were reacted while removing the resulting butanol under reduced pressure. Fourteen grams of butanol was recovered. As a result, there was obtained a titanium compound in which one half of the alkoxide had been substituted by 2-ethylhexanol. To the titanium compound, there were added a solution of 3 g (0.016 mole; OH equivalent: 0.1) in 20 g of butanol and another solution of 3.6025 g (0.2 mole; OH equivalent: 0.4) respectively. The resultant mixture was heated under reflux for 3 hours. The resulting butanol and 2-ethylhexanol were then distilled off under reduced pressure and the residue was then heated at 180° C. for 6 hours under 20 mmHg and for a further 30 minutes under 1 mmHg so that a polytitanic acid forming reaction was conducted. The reaction mixture was then heated for 30 minutes in butanol which contained 3.6 g of water and under reduced pressure, the reaction mixture was heated to remove the solvent, thereby obtaining 13.21 g of a solid catalyst. In view of its stoichiometric yield, the solid catalyst still contained terminal alkoxy groups.

Then, 0.8027 g of the above prepared solid catalyst was added to a mixture of 74 g (0.5 mole) of phthalic anhydride and 163 g (1.25 moles) of octanol to conduct a dehydration and esterification reaction. Water was distilled to one half of its stoichiometric amount within 30 minutes and to the stoichiometric amount within 65 minutes. The acid value was 0.13 two and a half hours later and 0.04 five hours later.

EXAMPLE 22

To 28.4 g (0.1 mole; isopropoxy equivalent: 0.4) of tetraisopropoxy titanium, an isopropanol solution of 1.8008 g (0.1 mole; OH equivalent: 0.2) of water was added under cooling. Some undissolved matter, which rendered the reaction mixture cloudy, was dissolved while heating the reaction mixture. After heating the reaction mixture for 30 minutes, it was cooled again and the remaining portion, i.e., 1.7820 g (0.1 mole; OH equivalent: 0.2) of water was added. The reaction mixture was in a liquid form in the beginning but a precipitate was crystallized out as the temperature went up. A gel-like precipitate was crystallized out at 40° C. After distilling off isopropanol, butanol was added to the residue. The resultant mixture was heated under reflux for 8 hours and the solvent was caused to evaporate completely. A solid substance was then obtained. The solid substance was again heated for 30 minutes in butanol which contained 3.0 g of water, whereby the solid substance was subjected to hydration. The thus-hydrated reaction product was collected by filtration and was then dried. Using the above-prepared solid catalyst, an esterification and ester interchange reaction of adipic acid, a diol and a monohydric alcohol was conducted as will be described next.

Namely, to a mixture of 146 g (1 mole) of adipic acid, 36 g (0.4 mole) of 1,4-butanediol and 104 g (0.8 mole) of 2-ethylhexanol, 0.5004 g of the above-prepared solid catalyst was added to conduct a dehydration and esterification reaction. Within 25 minutes, 15 ml of water was distilled out so that the conversion was 40%. From this time point, the dropwise addition of the remaining portion, i.e., 104 g (0.8 mole) of 2-ethylhexanol was started. The addition was completed before attainment of a conversion of 80%, in other words, within 60 minutes. During the addition, the dehydration and esterification reaction proceeded smoothly at 190°-200° C. Approximately the stoichiometric amount, namely, 36 ml of water was distilled within 1.5 hours. The acid value of the product of the esterification reaction dropped to 0.25 two and a half hours later, to 0.06 four hours later and further to 0.03 five hours later. After the esterification, the composition of the ester mixture having the low acid value was theoretically found from the above-described molar ratio of the reactants to correspond to that of a mixture composed of 0.6 mole of DOA and 0.4 mole of an ester alcohol (octyl on one side and 1,3-butanediol ester on the other hand). When this mixture of the ester alcohol and diester was heated at 180°-190° C. under reduced pressure, i.e., at 20 mmHg-1 mmHg, the removal of 2-ethylhexanol proceeded and 51 g of 2-ethylhexanol was recovered almost stoichiometrically. It was hence found that the above-prepared dehydration and esterification catalyst functioned as an esterification catalyst. The reaction product showed an acid value of 0.04. After removal of the catalyst, the reaction mixture was distilled to remove DOA. The principal component of the thus-prepared mixed ester was 1,3-butanediol bis-2-ethylhexyl adipate. The mixed ester was a mixture of the principal component and two to three oligomers. When the mixed ester was used as a plasticizer for a polyvinyl chloride resin, the mixed ester exhibited substantially the same degree of plasticity as DOP and hence provided a plasticized polyvinyl chloride sheet which had excellent heat resistance as demonstrated by substantially no loss of the mixed ester on heating over a long period of time (heating at 100° C. for 1,500 hours).

EXAMPLE 23

Added to 28.4 g (0.1 mole) of tetraisopropyl titanate was 42 g (0.4 mole) of 2-ethylhexanol. The resultant mixture was heated at 160°-180° C. The resultant isopropyl alcohol was distilled off, thereby tetraoctyl titanate was synthesized. This reaction mixture was then mixed with 20 g of "Chromosorp W" (trade name; product of Gasukuro Kogyo Inc.; carrier produced from diatomaceous earth as a raw material). The resultant mixture was cooled with stirring, to which 50 g of isopropanol with 1.7952 g of water incorporated therein was added. The thus-prepared mixture was heated under reflux for 1 hour, thereby distilling off isopropanol. The residue was cooled again. In exactly the same manner, 50 g of isopropanol with 1.8008 g of water incorporated therein was added. The temperature of the resultant mixture was raised gradually. After eventual distillation of isopropanol, 20 g of fresh 2-ethylhexanol was added and the reaction mixture was heated at 160°-180° C. for 16 hours. After collecting the reaction product by filtration and washing same, 100 g of butanol with 3.6 g of water incorporated therein was added to the reaction product. After heating the mixture for 30 minutes, the reaction product was collected by filtration and then washed. It was then dried under reduced pressure to obtain 29.5 g of a carrier-borne catalyst. The carrier-borne catalyst was added as a catalyst to a mixture of 148 g (1 mole) of phthalic anhydride and 273 g (2.1 moles) of 2-ethylhexanol to conduct a dehydration and esterification reaction. Water was distilled to one half of its stoichiometric amount within 20 minutes and approximately to the stoichiometric amount within 55 minutes. The acid value was found to be 0.16 one hour and a half later, 0.08 two hours later and 0.04 three hours later. The reaction mixture remained clear until the end of the experiment. DOP of a low acid value was obtained by decantation. Owing to the preparation of the catalyst on the carrier, the filtration of the catalyst was extremely facilitated. (Examples on Polyol Polytitanic Acids Containing The Polytitanic Acid Structure)

EXAMPLE 24

Added to a liquid mixture of 39 g (0.3 mole) of 2-ethylhexanol and 4.5 g (0.033 mole) of trimethylolpropane was 34 g (0.1 mole) of tetrabutyl titanate (tetrabutoxy titanium). The resultant mixture was heated at 180° C. to dissolve the trimethylol propane. Thereafter, the resultant solution was heated under reduced pressure, i.e., 25 mmHg. Butanol was distilled almost stoichiometrically, namely, in a total amount of 29 g (0.4 mole). The thus-obtained titanate solution was allowed to cool down to room temperature, to which a solution of 0.9005 g (0.05 mole) of water in 20 g of butanol was added little by little with stirring. The resulting mixture was then heated to drive off butanol. Under reduced pressure, the resulting 2-ethylhexanol was also removed by distillation so that an oily viscous substance was obtained. This product was also allowed to cool down to room temperature and was then diluted with 50 g of butanol. When 20 g of butanol with 0.4500 g (0.025 mole) of water incorporated therein was added, a precipitate started to occur in the course of the addition. The resulting mixture was then heated at 180° C. and while removing butanol and the resulting 2-ethylhexanol under reduced pressure (25-2 mmHg), a crosslinking reaction was conducted sufficiently. After the crosslinking reaction, 50 g of water-saturated butanol was added and the resulting mixture was maintained at 100° C. for 30 minutes to conduct an activation treatment. The reaction product was then collected by filtration and washed with water, and thereafter dried under reduced pressure to obtain 13.5 g of a solid catalyst.

Then, 0.8 g of the above prepared solid catalyst was added to a mixture of 74 g (0.5 mole) of phthalic anhydride and 163 g (1.25 moles) of 2-ethylhexanol and in the presence of a small amount of toluene, a dehydration and esterification reaction was conducted at 190°-215° C. One hour later, the acid value of the product of the esterification reaction was 0.16. Water was distilled substantially to its stoichiometric amount within one hour and a half. The acid value dropped to 0.06 two hours later and further to 0.03 three hours later. The catalyst residue was removed by filtration, and remaining 2-ethylhexanol was distilled off under reduced pressure to obtain DOP (dioctyl phthalate) having a small acid value.

(Comparative Example)

Dissolved in 10 g of butanol was 17 g (0.05 mole) of butyl titanate. While adding a mixture of 1.8 g (0.1 mole) of water and 20 g of butanol little by little, the temperature of the reaction mixture was heated to 100°-120° C. and a polymerization and crosslinking reaction was conducted for 1 hour, thereby preparing a polytitanate. Three hours later, the resultant butanol was distilled off and the residue was then heated at 180°-190° C. under reduced pressure (25-1 mmHg) to achieve its crosslinking to a sufficient degree. A liquid mixture of 0.8 g of water and 20 g of butanol was then added and the resulting mixture was allowed to stand overnight. After heating the mixture at 100° C. for 1 hour and activating the reaction product, the solvent and butanol were distilled off under reduced pressure to obtain 5.2 g of a solid catalyst.

To a mixture of 146 g (1 mole) of adipic acid and 325 g (2.5 moles) of 2-ethylhexanol, 0.5 g of the above-prepared solid catalyst was then added and in the presence of a small amount of toluene, a dehydration and esterification reaction was conducted at 180°-200° C. The acid value dropped to 0.08 two hours later and further to 0.04 three hours later.

Furthermore, 0.5 g of the above-prepared solid catalyst was also added to a mixture of 146 g (1 mole) of phthalic acid and 325 g (2.5 moles) of 2-ethylhexanol to conduct a dehydration and esterification reaction in the same manner. As a result, the stoichiometric amount of water was distilled within 4 hours. However, the acid value was 3.35 at that time. The acid value dropped to 0.15 eight hours later and 0.02 twelve hours later. This indicates that the above-prepared solid catalyst was able to achieve substantially the same reaction velocity as the catalyst of Example 24 when the acid was adipic acid but the reaction velocity was significantly slower in the case of phthalic acid.

EXAMPLE 25

To a liquid mixture of 39 g (0.3 mole) of 2-ethylhexanol and 3.4 g (0.025 mole) of pentaerythritol, 28.4 g (0.1 mole) of tetraisopropyl titanate (tetraisopropyloxy titanium) was added. The resulting mixture was heated at 180° C. at normal pressure and then under reduced pressure, thereby distillating off 23.5 g (0.4 mole) of isopropanol. At room temperature, 20 g of isopropanol with 1.800 g (0.1 mole) of water incorporated therein was added little by little to the reaction product, i.e., pentaerythritol-2-ethylhexanol titanate. Thereafter, the resultant mixture was heated at 180° C. to drive off isopropanol. The resultant 2-ethylhexanol was then distilled off under reduced pressure (25 mmHg), thereby obtaining an oily viscous substance which contained a small amount of solids. Fifty grams of isopropanol with 0.9002 g (0.05 mole) of water incorporated therein was again added little by little with stirring, whereby some solid was allowed to crystallize out. The reaction mixture was then subjected to a heat treatment at 180° C. and isopropanol and 2-ethylhexanol were removed under reduced pressure, i.e., 25-2 mmHg. After completion of the reaction, 50 g of water-saturated butanol was added. The resultant mixture was maintained at 100° C. for 30 minutes. The reaction product was collected by filtration and then washed with isopropanol, followed by its drying under reduced pressure to obtain 12.4 g of a solid catalyst.

In much the same way as in Example 24, 0.8 g of the above-prepared solid catalyst was added to a mixture of 0.5 mole of phthalic anhydride and 1.25 mole of 2-ethylhexanol to conduct a dehydration and esterification reaction. The acid value dropped to 0.4 two hours later and further to 0.03 three hours later. After completion of the dehydration and esterification reaction, the catalyst was filtered off and excess 2-ethylhexanol was distilled off, thereby obtaining DOP having an acid value of 0.04.

EXAMPLE 26

To 50 g (0.18 mole) of dibutyl adipate (DBA), 49 g (0.5 mole) of maleic anhydride and 45 g (0.5 mole) of 1,3-butanediol were added. The resultant mixture was stirred at 60° C. to have the acid anhydride react thoroughly. After the proportion of the acid anhydride was confirmed to have dropped to 2% by titration (4 hours later), 219 g (1.5 moles) of adipic acid, 0.7983 g of the solid catalyst prepared in Example 25 and 37 g of butanol were added to initiate a dehydration and esterification reaction. The dehydration and esterification reaction was conducted by heating the reaction system at 180°–200° C. while adding a stoichiometric amount (222 g) of butanol in portions corresponding to the amount of distilled water. The reduction of the acid value was approximately proportional to the logarithm of the concentration of the acid. It was found to be 29.9 two hours later, 14.2 three hours later, 8.9 four hours later, 3.7 five hours later, 0.51 six hours later and 0.30 seven hours later. Although the above esterification is a reaction for the formation of a butyl ester, a small acid value was achieved very promptly. Butanol was distilled off from the reaction product, followed by an ester interchange reaction and removal of volatile butanol. The catalyst was thereafter filtered off. The filtrate was then mixed with 5 ml of water at 100° C. and was washed with aqueous alkaline solution and hot water to lower the acid value significantly. The filtrate was then distilled under reduced pressure to obtain 80 g of a product, which was composed principally of 1,3-butanediol butyl adipate butyl maleate and had a boiling point of 230°–238° C./0.4 mmHg (viscosity: 45 cps at 21° C.), and 80 g of a liquid residue composed of low-molecular oligomers (viscosity: 134 cps at 21° C.). This dehydration and esterification reaction is intended to conduct the preparation of 1,3-butanediol butyl adipate butyl maleate as an intended product while forming DBA in an excess amount. Production of such a complex mixed ester has been rendered feasible for the first time owing to the use of the solid catalyst of this invention which can achieve a small acid value in a short period of time. In the course of the reaction, an ester interchange reaction takes place between 1,3-butanediol butyl maleate, which occurs in a small amount as a byproduct, and DBA, thereby making it possible to form the intended product.

Incidentally, 18 hours are required to reduce the acid value to 0.6 when esterification is conducted by using tetrabutoxy titanium as a catalyst. In this case, the esterification reaction is effected for many hours. As a result, unnecessary ester interchange reactions are also allowed to proceed. As a consequence, extremely little compound is obtained by distillation. The viscosity of the reaction mixture is as high as 1070 cps. This indicates that the conversion into polyesters has proceeded.

In an esterification reaction making use of p-toluenesulfonic acid as a catalyst, the acid value does not drop below 2. Extreme difficulties are hence encountered upon separating of the reaction product from water by washing the reaction mixture with an alkaline solution. It is thus impossible to obtain an ester of a small acid value. It was also unable to obtain pure products by distillation.

EXAMPLE 27

A liquid mixture of 28.4 g (0.1 mole) of tetraisopropyl titanate, 4.5 g (0.033 mole) of trimethylolpropane, 0.1 g (0.0004 mole) of stearyl alcohol and an excess amount, i.e., 100 g (1.37 moles) of butanol was heated under reflux to dissolve the solid substance completely. The resultant isopropyl alcohol and butanol were then distilled off to obtain trimethylolpropane-butyl alcohol-titanate (polyol titanate). The polyol titanate was then cooled by ice, followed by an addition of butanol which contained 1.8002 g (0.10 mole) of water. After heating the resultant mixture to form a uniform solution, butanol was removed by distillation. Under cooling, butanol with 0.9005 g (0.05 mole) of water incorporated therein was added again. The resultant mixture was heated to effect polymerization and crosslinking. Butanol was then removed thoroughly under reduced pressure. After heating the residue again at 100° C. for 30 minutes in water-containing butanol, the product was dried under reduced pressure to obtain 12.2 g of a solid substance. This solid substance had such properties that it showed water repellency when water was added thereto but its surface was wet immediately when an alcohol was added thereto.

To a mixture of 146 g (1 mole) of adipic acid and 325 g (2.5 moles) of 2-ethylhexanol, 0.8 g of the above-prepared solid catalyst was added. When a dehydration and esterification reaction was carried out at 180°–200° C. in the presence of a small amount of toluene, the acid value dropped to 0.06 two hours later and further to 0.04 three hours later. The catalyst was filtered off and excess 2-ethylhexanol was distilled off under reduced pressure, thereby obtaining dioctyl adipate (DOA) having a small acid value. When an esterification reaction of phthalic anhydride was conducted by using the same catalyst, the acid value was 1.50 five hours later. It took 8 hours until the acid value dropped to 0.04. This indicates that the catalyst of this invention has selectivity in the degree of its activities for acids employed in esterification reactions.

EXAMPLE 28

Added to 34 g (0.1 mole) of tetrabutoxy titanium was a liquid mixture of 13 g (0.1 mole; OH equivalent: 0.1) of 2-ethylhexanol and 13.5 g (0.15 mole; OH equivalent: 3) of 1,4-butanediol. The resultant mixture was heated over an oil bath of 180° C. Six hours later, 29.0 g (0.4 mole) of the resultant butanol was distilled off under reduced pressure. The reaction product was in the form of a viscous liquid. To the viscous liquid, 29 g of butanol with 0.900 g (0.05 mole) of water incorporated therein was added at room temperature. The resultant mixture was heated at 180° C. under reflux, thereby allowing some solid product to crystallize out. When the thus-formed 2-ethylhexanol was distilled off while heating the reaction mixture under reduced pressure, a colorless solid product was obtained. Fifty grams of water-saturated butanol was then added and the resulting mixture was maintained with stirring at 80° C. for 1 hour. It was thereafter filtered to collect a solid substance. The solid substance was then dried under reduced pressure to obtain 18.5 g of a solid catalyst. Similar to Example 24, 0.8 g of the above-prepared solid catalyst was added to a mixture of 0.5 mole of phthalic anhydride and 1.25 moles of 2-ethylhexanol to conduct a dehydration and esterification reaction. Three hours later, the acid value was found to be 0.08.

EXAMPLE 29

Thirty-four grams (0.1 mole) of tetrabutoxy titanium was added to a mixture of 26 g (0.2 mole; OH equivalent: 2) of 2-ethylhexanol and 8.8 g (OH equivalent: 2) of powdery polyvinyl alcohol (average molecular weight: 500). The resultant mixture was heated under reflux for 8 hours over an oil bath of 180° C. After distilling off 14 g (0.2 moles) of the resulting butanol, a liquid mixture of 1.8 g (0.1 mole; OH equivalent: 2) of water and butanol was added at room temperature. The thus-prepared mixture was again heated at 180° C. for 6 hours over an oil bath. A volatile oil fraction was then distilled off under reduced pressure (2–3 mmHg). Fifty grams of watersaturated butanol were added again and the resulting mixture was heated with stirring at 80°–90° C. The reaction product was then collected by filtration. It was dried under reduced pressure to provide a solid catalyst. Similar to Example 24, a preparation experiment of 0.5 mole of DOP was conducted at a reaction temperature of 190°–220° C. by using 1.0 g of the above-prepared catalyst. Three hours later, the acid value was found to be 0.10.

EXAMPLE 30

To 34 g (0.1 mole) of tetrabutoxyethane, 52 g (0.4 mole) of 2-ethylhexanol was added. The resultant mixture was heated at 180° C., followed by distillation of 29 g (about 0.4 mole) of the resultant butanol under reduced pressure (25 mmHg) to obtain tetra-2-ethylhexyloxy titanium. After an addition of 20 g of butanol with 0.900 g (0.05 mole) of water incorporated therein, the resultant mixture was heated to drive off butanol. Thereafter, 13 g of the resultant 2-ethylhexanol was distilled off under reduced pressure, i.e., 25 mmHg. Then, 4.5 g (0.03 mole) of trimethylolpropane was added and the thus-obtained mixture was heated for 8 hours over an oil bath of 180° C. Although trimethylolpropane was dissolved gradually, a solid substance was crystallized out finally. After an addition of a solution of 0.45 g (0.025 mole) of water in 20 g of butanol, the resulting mixture was again heated at 180° C. and the resultant 2-ethylhexanol was distilled off under reduced pressure (25–2 mmHg). Fifty grams of butanol with 3 g of water incorporated therein were again added and the resultant mixture was heated for 1 hour at 80°–100° C. to conduct its hydrolysis. The reaction product was collected by filtration and was then dried under reduced pressure to remove the volatile component (ethylhexanol) until the weight became constant, thereby obtaining 13.8 g of a solid product.

To a mixture of 74 g (0.5 mole) of phthalic anhydride and 163 g (1.25 mole) of 2-ethylhexanol, 0.8 g of the above-prepared solid catalyst was added. A dehydration and esterification reaction was then conducted at 190°–215° C. The acid value of the product of the esterification reaction was 2.1 one hour later and 0.04 three hours later. Thus, the reaction velocity was significantly high. Thereafter, the reaction mixture was filtered to remove the catalyst residue. By removing excess 2-ethylhexanol under reduced pressure, there was obtained DOP having a small acid value of 0.04.

Having now fully described the invention, it will be apparent to one of ordinary skill in the art that many changes and modifications can be made thereto without departing from the spirit or scope of the invention as set forth herein.

What is claimed is:

1. A process for the preparation of a highly-crosslinked polyol polytitanate useful as an esterification and/or ester interchange catalyst, which process comprises the steps of heating an alkoxy titanium with a polyol to form a reaction product, de-alcoholizing the reaction product by heating the reaction product under reduced pressure to form a highly-crosslinked high-molecular solid product, and treating the solid product with water to convert the solid product to a hydrate and activate is surface.

2. The process as claimed in claim 1, wherein the alkoxy titanium and the polyol are reacted in the presence of a carrier.

3. The process as claimed in claim 2, wherein the carrier is selected from the group consisting of silica, alumina, zeolite, a molecular sieve and activated carbon.

4. The process as claimed in claim 1, wherein the polyol and the alkoxy titanium are reacted at a molar ratio (polyol/alkoxy titanium) in the range of (0.9–1.8-)×a/b in which a is the number of alkoxy groups per molecule of the alkoxy titanium and b is the number of OH groups per molecule of the polyol.

5. The process as claimed in claim 1, wherein the alkoxy titanium is obtained by adding a higher alcohol to an alkoxy titanium of a lower alcohol and then heating the resultant mixture.

6. A process for the preparation of an esterification and/or ester interchange catalyst comprising a highly-crosslinked high-molecular polytitanate, which process comprises the steps of heating an alkoxy titanium with water to form a reaction product, de-alcoholizing the reaction product by heating under reduced pressure to form a highly-crosslinked high-molecular solid product, and treating the solid product with water to convert the solid product to a hydrate and activate its surface.

7. The process as claimed in claim 6, wherein the alkoxy titanium and water are reacted in the presence of a carrier.

8. The process as claimed in claim 7, wherein the carrier is selected from the group consisting of silica, alumina, zeolite, a molecular sieve and activated carbon.

9. The process as claimed in claim 6, wherein the water and alkoxy titanium are reacted at a molar ratio (water/alkoxy titanium) in the range of (1–2)×a/2 in which a is the number of alkoxy groups per molecule of the alkoxy titanium and wherein water acts as a diacidic base.

10. The process as claimed in claim 6, wherein the alkoxy titanium is obtained by reacting a higher alcohol with an alkoxy titanium of a lower alcohol.

11. A process for the preparation of an esterification and/or ester interchange catalyst comprising a polyol polytitanate having the polytitanic acid structure, which process comprises the steps of heating the reaction product of an alkoxy titanium and a polyol or water with water or a polyol, respectively, to form a new reaction product, de-alcoholizing the new reaction product by heating the new reaction product under reduced pressure to form a highly-crosslinked high-molecular solid product, and treating the solid product with water to convert the solid product to a hydrate and activate its surface.

12. The process as claimed in claim 11, wherein the alkoxy titanium is obtained by reacting a higher alcohol with an alkoxy titanium of a lower alcohol.

13. A process for the preparation of an esterification and/or ester interchange catalyst comprising a polyol polytitanate having the polytitanic acid structure, which process comprises the steps of heating the reaction product of an alkoxy titanium of a lower alcohol, a monohydric higher alcohol and a polyol with water to form a new reaction product, de-alcoholizing the new reaction product by heating the new reaction product under reduced pressure to obtain a highly-crosslinked highmolecular solid product, and treating the solid product with water to convert the solid product to a hydrate and activate its surface.

14. The process as claimed in any one of claims 1, 6, 11 and 13, wherein the highly-crosslinked solid product is treated with a solvent to remove less active soluble matter therefrom before the water treatment of the highly-crosslinked product.

15. A highly-crosslinked polyol polytitanate useful as an esterification and/or ester interchange catalyst prepared according to the process which comprises the steps of heating an alkoxy titanium with a polyol to form a reaction product, dealcoholizing the reaction product by heating the reaction product under reduced pressure to form a highly-crosslinked highmolecular solid product, and treating the solid product with water to convert the solid product to a hydrate and activate its surface, said highly-crosslinked polyol polytitanate being insoluble in esterification and ester interchange reactions.

16. An esterification and/or ester interchange catalyst comprising a highly-crosslinked high-molecular polytitanate prepared according to the process which comprises the steps of heating an alkoxy titanium with water to form a reaction product, de-alcoholizing the reaction product by heating under reduced pressure to form a highly-crosslinked high-molecular solid product, and treating the solid product with water to convert the solid product to a hydrate and activate is surface, said catalyst being insoluble in esterification and ester interchange reactions.

17. An esterification and/or ester interchange catalyst comprising a polyol polytitanate having the polytitanic acid structure prepared according to the process which comprises the steps of heating the reaction product of an alkoxy titanium and a polyol or water with water or a polyol, respectively, to form a new reaction product, de-alcoholizing the new reaction product by heating the new reaction product under reduced pressure to form a highly-crosslinked high-molecular solid product, and treating the solid product with water to convert the solid product to a hydrate and activate its surface, said catalyst being insoluble in esterification and ester interchange reactions.

18. An esterification and/or ester interchange catalyst comprising a polyol polytitanate having the polytitanic acid structure prepared according to the process which comprises the steps of heating the reaction product of an alkoxy titanium of a lower alcohol, a monohydric higher alcohol and a polyol with water to form a new reaction product, de-alcoholizing the new reaction product by heating the new reaction product under reduced pressure to obtain a highly-crosslinked high molecular solid product, and treating the solid product with water to convert the solid product to a hydrate and activate its surface, said catalyst being insoluble in esterification and ester interchange reactions.

* * * * *